US008367378B2

(12) United States Patent
Balan et al.

(10) Patent No.: US 8,367,378 B2
(45) Date of Patent: Feb. 5, 2013

(54) PROCESS FOR PRODUCING SUGARS AND ETHANOL USING CORN STILLAGE

(75) Inventors: Venkatesh Balan, East Lansing, MI (US); Shishir Chundawat, East Lansing, MI (US); Leonardo Sousa, Lansing, MI (US); Bruce Dale, Mason, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 952 days.

(21) Appl. No.: 12/286,913

(22) Filed: Oct. 3, 2008

(65) Prior Publication Data

US 2009/0093027 A1 Apr. 9, 2009

Related U.S. Application Data

(60) Provisional application No. 60/997,458, filed on Oct. 3, 2007.

(51) Int. Cl.
*C12P 19/14* (2006.01)
*C12P 7/10* (2006.01)

(52) U.S. Cl. .......................................... 435/99; 435/165
(58) Field of Classification Search ........................ None
See application file for complete search history.

(56) References Cited

U.S. PATENT DOCUMENTS

| | | | |
|---|---|---|---|
| 4,263,744 A | 4/1981 | Stoller | |
| 4,370,351 A | 1/1983 | Harper | |
| 4,526,791 A | 7/1985 | Young | |
| 4,600,590 A | 7/1986 | Dale | |
| 4,624,805 A | 11/1986 | Lawhon | |
| 4,644,060 A | 2/1987 | Chou | |
| 4,848,026 A | 7/1989 | Dunn-Coleman et al. | |
| 5,037,663 A | 8/1991 | Dale | |
| 5,047,332 A | 9/1991 | Chahal | |
| 5,171,592 A | 12/1992 | Holtzapple et al. | |
| 5,473,061 A | 12/1995 | Bredereck et al. | |
| 5,736,032 A | 4/1998 | Cox et al. | |
| 5,865,898 A | 2/1999 | Holtzapple et al. | |
| 5,939,544 A | 8/1999 | Karstens et al. | |
| 6,106,888 A | 8/2000 | Dale et al. | |
| 6,176,176 B1 | 1/2001 | Dale et al. | |
| 6,416,621 B1 | 7/2002 | Karstens | |
| 6,444,437 B1 | 9/2002 | Sporleder et al. | |
| 7,049,485 B2 | 5/2006 | Stricklen et al. | |
| 7,371,962 B2 | 5/2008 | Zuppero et al. | |
| 7,494,675 B2 * | 2/2009 | Abbas et al. | 426/12 |
| 7,910,338 B2 * | 3/2011 | Hennessey et al. | 435/99 |
| 7,915,017 B2 | 3/2011 | Dale | |
| 2003/0044951 A1 | 3/2003 | Sporleder et al. | |
| 2005/0233423 A1 | 10/2005 | Berka et al. | |
| 2006/0177917 A1 | 8/2006 | Warzywoda et al. | |
| 2007/0031918 A1 | 2/2007 | Dunson, Jr. et al. | |
| 2007/0192900 A1 | 8/2007 | Sticklen | |
| 2007/0227063 A1 | 10/2007 | Dale et al. | |
| 2007/0287795 A1 | 12/2007 | Huda et al. | |
| 2008/0008783 A1 | 1/2008 | Dale | |
| 2009/0011474 A1 | 1/2009 | Balan et al. | |
| 2009/0042259 A1 | 2/2009 | Dale et al. | |
| 2009/0053771 A1 | 2/2009 | Dale et al. | |
| 2009/0061486 A1 | 3/2009 | Edwards et al. | |
| 2009/0093027 A1 | 4/2009 | Balan et al. | |
| 2009/0178671 A1 | 7/2009 | Ahring et al. | |
| 2009/0221042 A1 | 9/2009 | Dale et al. | |
| 2009/0318670 A1 | 12/2009 | Dale et al. | |
| 2010/0267999 A1 | 10/2010 | Lau et al. | |
| 2011/0192559 A1 | 8/2011 | Venkatesh et al. | |
| 2011/0201091 A1 | 8/2011 | Dale | |
| 2011/0300269 A1 | 12/2011 | Dale et al. | |
| 2012/0125548 A1 | 5/2012 | Cohen | |
| 2012/0125551 A1 | 5/2012 | Cohen et al. | |

FOREIGN PATENT DOCUMENTS

| | | |
|---|---|---|
| DE | 20301645 | 4/2003 |
| EP | 1247781 A2 | 10/2002 |
| IN | 249187 | 10/2011 |
| RU | 22157655 C1 | 11/2003 |
| WO | WO-2007005918 A2 | 1/2007 |
| WO | WO 2007/130337 | 11/2007 |
| WO | WO-2007130337 A1 | 11/2007 |
| WO | WO 2008/020901 | 2/2008 |
| WO | WO-2008020901 A2 | 2/2008 |
| WO | WO-2009045527 A1 | 4/2009 |
| WO | WO-2011028543 A2 | 3/2011 |

OTHER PUBLICATIONS

"U.S. Appl. No. 12/226,850, Restriction Requirement mailed Jun. 30, 2011", 4 pgs.
Balan, V., et al., "Mushroom spent straw: a potential substrate for an ethanol-based biorefinery", J Ind Microbiol Biotechnol., 35(5), (May 2008), 293-301.
Baldrian, P, et al., "Variability of laccase activity in the white-rot basidiomycete*Pleurotus ostreatus*", Folia Microbiologica, 47, (2002), 385-90.
Chahal, D S, "Bioconversion of hemicelluloses into useful products in an integrated process for food/feed and fuel (ethanol) production from biomass", Research Org, Univ. de Quebec, Canada., (1984), 355-61.
Chang, Shu-Ting, "The World Mushroom Industry: Trends and Technological Development", International Journal of Medicinal Mushrooms, 8(4), (2006), 297-314.
Christian, V, et al., "Degradation of xenobiotic compounds by lignin-degrading white-rot fungi: enzymology and mechanisms involved", Indian Journal of Experimental Biology, 43, (Apr. 2005), 301-312.
Cohen, "Biotechnological applications and potential of wood-degrading mushrooms of the genus *Pleurotus*", Appl Microbiol Biotechnol, 58, (2002), 582-94.
De Ferrer, B Sulbaran, et al., "No. 6. Sugar production from rice straw", Arch. Latinoam. Prod. Anim., 5(Supl.1), (1997), 112-114.
Ferrer, A, et al., "Increasing nutrient availability of feather meal for ruminants and non-ruminants using an ammonia pressurisation/depressurisation process", Journal of the Science of Food and Agriculture, 79, (May 1999), 828-32.

(Continued)

*Primary Examiner* — Tekchand Saidha
*Assistant Examiner* — Younus Meah
(74) *Attorney, Agent, or Firm* — Clark IP Law, PLC

(57) ABSTRACT

A process for producing sugars from lignocellulosic materials such as corn stover by the addition of corn stillage as a carbon source is disclosed. The sugars are formed by treating the combination of the corn stillage and the lignocellulosic materials with hydrolytic enzymes. The sugars can be fermented to ethanol, and the process improves ethanol production economies with an increased sugar yield from the lignocellulosic materials.

29 Claims, 11 Drawing Sheets

OTHER PUBLICATIONS

Gollapalli, L. E, et al., "Predicting digestibility of ammonia fiber explosion (AFEX) treateii rice straw", Appl Biochem Biotech, (2002), 98-100.

Houghton, et al., "Fungal upgrading of wheat straw for straw-thermoplastics production", Applied Biochemistry and Biotechnology, vol. 113-116, (2004), 71-93.

Israelides, Cleanthes, "Bio-technologies of recycling agro-industrial wastes for the production of commercially important fungal polysaccharides and mushrooms.", Biotechnol Genet Eng Rev, 20, (2003), 247-59.

Karunanandaa, "Botanical fractions of rice straw colonized by white-rot fungi: changes in chemical composition and structure", Animal Feed Science and Technology, 55(3), (Oct. 1995), 179-99.

Kellar, Fred A, et al., "Microbial pretreatment of biomass", Applied Biochemical Biotechnology, (Spring 2003), 27-41.

Martinez, Angel T, et al., "Biodegradation of lignocellulosics: microbial, chemical, and enzymatic aspects of the fungal attack of lignin", International Microbiology, 8, (2005), 195-204.

Obodai, "Comparative study on the growth and yield of *Pleurotus ostreatus* mushroom on different lignocellulosic by-products", J Ind Microbiol Biotechnol, 30, (2003), 146-9.

O'Connor, "Ammonia explosion pulping—a new fiber separation process", Tappi, 55(3), (Mar. 1972).

Poppe, J, "Use of agricultural waste materials in the cultivation of mushrooms", In Science and cultivation of edible fungi. Proceedings of the 15th International Congress on the Science and Cultivation of Edible Fungi, Maastricht, Netherlands, May 15-19, 2000., (2000), 9-23.

Sanchez, Alfonso, "Biodegradation of Viticulture Wastes by *Pleurotus*: A Source of Microbial and Human Food and Its Potential Use in Animal Feeding", Journal of Agriculture and Food Chemistry, (2002), 2537-42.

Sarikaya, Ayda, et al., "Solid-state fermentation of lignocellulosic plant residues from *Brassica napus* by *Pleurotus ostreatus*", Appl Biochem Biotechnol., 82(1), (Oct. 1999), 1-15.

Singh, Anshu, et al., "Composting of a crop residue through treatment with microorganisms and subsequent vermicomposting", Bioresouce Technology, 85, (2002), 107-11.

Taniguchi, Masayuki, et al., "Evaluation of pretreatment with *Pleurotus ostreatus* for enzymatic hydrolysis of rice straw", Journal of Bioscience and Bioengineering, 100(6), (Dec. 2005), 637-643.

Teymouri, Farzaneh, et al., "Optimization of the ammonia fiber explosion (AFEX) treatment parameters for enzymatic hydrolysis of corn stover", Bioresource Technology, 96, (2005), 2014-18.

Turner, N D, et al., "Disruption of forage structure with an ammonia fiber explosion process", Proceedings, Western Section, American Society of Animal Science, 41, (1990), 794-97.

Williams, B C, et al., "An initial assessment of spent mushroom compost as a potential energy feedstock", Bioresource Technology, 79, (2001), 227-30.

Wyman, Charles E, et al., "Comparative sugar recovery data from laboratory scale application of leading pretreatment technologies to corn stover", Bioresource Technology, 96, (2005), 2026-32.

Wyman, Charles E, et al., "Coordinated development of leading biomass pretreatment technologies", Bioresour Technol., 96(18), (Dec. 2005), 1959-66.

Zhang, Ruihong, et al., "Oyster mushroom cultivation with rice and wheat straw", Bioresour Technol., 82(3), (May 2002), 277-84.

"U.S. Appl. No. 11/901,336, Response to Restriction Requirement mailed Mar. 11, 2010", 9 pgs.

"U.S. Appl. No. 11/901,336, Non Final Office Action mailed Apr. 27, 2010", 10 pgs.

"U.S. Appl. No. 11/901,336, Notice of Allowance mailed Aug. 24, 2010", 5 pgs.

"U.S. Appl. No. 11/901,336, Response to Non Final Office Action mailed Apr. 27, 2010", 11 pgs.

"U.S. Appl. No. 11/901,336, Restriction Requirement mailed Mar. 11, 2010", 9 pgs.

"U.S. Appl. No. 12/214,687, Non Final Office Action mailed Jun. 2, 2011", 6 pgs.

"U.S. Appl. No. 12/226,763, Preliminary Amendment filed Dec. 16, 2008", 4 pgs.

"U.S. Appl. No. 12/229,225, Response Filed Jun. 6, 2011 to Restriction Requirement Received May 5, 2011", 10 pgs.

"U.S. Appl. No. 12/229,225, Restriction Requirement mailed May 5, 2011", 6 pgs.

"U.S. Appl. No. 12/976,344, Preliminary Amendment filed Apr. 27, 2011", 10 pgs.

"Australian Application Serial No. 2007248736, Australian Office Action mailed Dec. 1, 2009", 2 pgs.

"Australian Application Serial No. 2007248736, Response filed Mar. 24, 2010 to Australian Office Action mailed Dec. 1, 2009", 7 pgs.

"Canadian Application Serial No. 2,650,860, Office Action mailed May 12, 2011", 2 pgs.

"Energy Policy Act of 2005", Sec. 1501, 109th Cong., 1st Sess, (2005), 11 pgs.

"European Application Serial No. 07776479.3, Amendment (new claims) dated Dec. 16, 2010", 9 pgs.

"European Application Serial No. 07776479.3, Extended European Search Report mailed May 26, 2010", 6 pgs.

"From Niche to Nation: Ethanol Industry Outlook 2006", Renewable Fuels Association Washington DC, (2006), 24 pgs.

"Indian Application Serial No. 5933/CHENP/2008, Office Action mailed Oct. 29, 2010", English translation, 2 pgs.

"International Application Serial No. PCT/US2007/010410, International Search Report mailed Jun. 10, 2008", 1 pg.

"International Application Serial No. PCT/US2007/010410, International Written Opinion mailed Jun. 10, 2008", 4 pgs.

"International Application Serial No. PCT/US2007/010410, Preliminary Report on Patentability mailed Dec. 12, 2008", 5 pgs.

"International Application Serial No. PCT/US2007/010415, Preliminary Report on Patentability mailed Aug. 1, 2008", 7 pgs.

"International Application Serial No. PCT/US2007/10415, International Search Report mailed Oct. 11, 2007", 2 pgs.

"International Application Serial No. PCT/US2007/10415, Written Opinion mailed Sep. 17, 2007", 4 pgs.

"International Application Serial No. PCT/US2008/011488, International Search Report mailed Jan. 8, 2009", 1 pg.

"International Application Serial No. PCT/US2008/011488, International Written Opinion mailed Jan. 8, 2009", 5 pgs.

Alizadeh, Hasan, et al., "Pretreatment of Switchgrass by Ammonia Fiber Explosion", Applied Biochemistry and Biotechnology 121-124, (2005), 1133-1141.

Allan, G., et al., "Replacement of fish meal in diets for Australian silver perch, *Bidyanus bidyanus*:I. Digestibility of alternative ingredients", Aquaculture, 186, (2000), 293-310.

Bahar, H, et al., "Splitting tendency of cellulosic fibers", Part 2: Effects of fiber swelling in alkali solution Cellulose, 13, (2006), 403-409.

Beale, C V, "Leaf photosynthesis in the C4 grass Miscanthus xgiganteus, growing in the cool temperate climate of southern England", Journal of Experimental Botany, 47, (1996), 267-273.

Betschart, A., et al., "Extractability and Solubility of Leaf Protein", Agri. Food Chem. vol. 21(1), (1973), 60-65.

Boluk, Y, "Acid -base interactions and swelling of cellulose fiber in organic liquids", Cellulose, 12, (2005), 577-593.

Chundawat, S PS, et al., "Effect of Particle Size Based Seperation of Milled Corn Stover on AFEX Pretreatment and Enzymatic Digestibility", Bioeng. Biotechnol, (2007), 219-231.

Chundawat, Shishir Pratap Singh, "Ultrastructural and physicochemical modifications within ammonia treated lignocellulosic cell walls and their influence on enzymatic digestibility", Ph.D., Michigan State University, (2010), 469 pgs.

Clifton-Brown, J C, et al., "Performance of 15 Miscanthus genotypes at five sites in Europe", Agronomy J., 93, (2001), 1013-1019.

De La Rosa, Luis B, et al., "Integrated Production of Ethanol Fuel and Protein from Coastal Bermudagrass", Appl. Biochem. and Biotechnol. vol. 45-46, (1994), 483-497.

De Vrije, T, et al., "Pretreatment of miscanthus for hydrogen production by *Thermotoja elfi*", International Journal of Hydrogen Economy, 27, (2005), 1381-1390.

Eggeman, Tim I, et al., "Process and Economic Anaylsis of Pretreatment Technologies", Bioresource Technology, 96, (2005), 2019-2025.

El-Adaway, T., et al., "Nutritional potential and functional properties of sweet and bitter lupin seed protein isolates", Food Chem. vol. 74, (2001), 455-462.

Felix, A., et al., "In Vitro and In Vivo Digestibility of Soya-Bean Straw Treated with Various Alkalis", Anim. Prod, 51, (1990), 47-61.

Fernandez, S., et al., "Protein extraction from Atriplexlampa leaves: Potential use as forage for animals used for human diets", Plant Foods for Human Nutrition, vol. 54, (1999), 251-259.

Ferrer, Alexis, et al., "Optimizing Ammonia Pressurization/Depressurization Processing Conditions to Enhance Enzymatic Susceptibility of Dwarf Elephant Grass", Appl. Biochem. and Biotechnol. 84-86, (2000), 163-179.

Fiorentini, R., et al., "Pilot Plant Production of an Edible Alfalfa Protein Concentrate", J. Food Sci. vol. 46, (1981), 1514-1520.

Foster, B L, et al., "Enzymatic hydrolosis of ammonia treated sugar beet pulp", Apple Biochem Biotechnol, vol. 91-93, (2001), 269-282.

Greene, Nathanael, et al., "Growing Energy: How Biofuels can Help End America's Oil Dependence", Natural Resources Defense Council, (Dec. 2004), 86 pgs.

Heaton, E, et al., "A quantitative review comparing the yeilds of two canidate C-4 perennial biomass crops in relation to nitrogen, temperature and water", Biomass and Bioenergy, 27, (2004), 21-30.

Heaton, E A, et al., "Miscanthus for Renewable Energy Generation: European Union Experience and Projections for Illinois", Mitigation and Adaptation Strategies for Global Change, (2004), 433-451.

Holtzapple, Mark T, et al., "The Ammonia Freeze Explosion (AFEX) Process", Appl. Biochem. and Biotechnol. 2829, (1991), 59-74.

Jeoh, T, et al., "Cooperative and competative binding in synergistic mixtures of *Thermobifidia fusca* cellulases Cel5A, Cel6B, and Cel9A", Biotechnol Prog., 18, (2002), 760-769.

Kamm, B., et al., "Principles of Biorefineries", Appl Mircobiol Biotechnol., 64, (2004), 137-145.

Kim, S B, et al., "Enhancement of the enzymatic digestility of waste newspaper using Tween", Appl. Biochem. Biotechnol., 129-132, (2006), 486-495.

Knauf, M., et al., "Lignocellulosic Biomass Processing: A Perspective", Int. Sugar J.,106, (2004), 147-150.

Kudra, T., et al., "Superheating Steam Drying", Advanced Drying Technologies, New York, NY : Marcel Dekker, Inc., (2002), 81-111.

Lau, M., et al., "Comparing the fermentation performance of *Escherichia coli* KO11, *Saccharomyces cerevisiae* 424A(LNH-ST) and *Zymomonas mobilis* AX101 for cellulosic ethanol production", Biotechnology for Biofuels, 3, (May 27, 2010), 10 pgs.

Lin, Y., et al., "Ethanol Fermentation from Biomass Resources: Current State and Prospects", Appl Microbiol Biotechnol, 69, (2006), 627-642.

Lovrien, R., et al., "Assays for Total Protein", Current Protocols in Protein Science, 3.4.1-3.4.24, (1995), 24 pgs.

Madakadze, I., et al., "Cutting Frequency and Nitrogen Fertilization Effects on Yield and Nitrogen Concentration of Switchgrass in a short Season Area", Crop Sci. vol. 39, (1999), 552-557.

Mantanis, G I, et al., "Swellin of compressed cellulose fiber webs in organic liquids", Cellulose, vol. 2, (1995), 1-22.

Mosier, N, et al., "Features of promising technologies for pretreatment of lignocellulosic biomass", Biosource Technology, 96(6), (Apr. 2005), 673-686.

Ohara, H., "Biorefinery", Appl. Microbiol Biotechnol., 62, (2003), 474-477.

Ordonez, C., et al., "Obtaining a Protein Concentrate from Intergral Defatted Sunflower Flour", Bioresour. Technol. vol. 78, (2001), 187-190.

Pandey, A, et al., "Economic utilization of crop residues for value addition: a futuristic approach", J. Sci. Ind. Res., vol. 59, (2000), 12-22.

Park, S., et al., "Investigation and Optimization of the Factors Influencing Sorghum Protein Extraction", Agri. Food Chem. vol. 51, (2003), 7050-7054.

Ragauskas, A J, et al., "The Path Forward for Biofuels and Biomaterials", Science, vol. 311, (2006), 484-489.

Saha, B. C, "Hemicellulose Bioconversion", J. Ind Microbiol Biotechnol., 30, (2003), 279-291.

Sanderson, M. A, et al., "Switchgrass as a Sustainable Bioenergy Crop", Bioresource Technology 56, (1996), 83-93.

Sluiter, A, et al., "Determination of Structural Carbohydrates and Lignin in Biomass", National Renewable Energy Laboratory, Technical Report NREL/TP-510-42618, Revised Jun. 2010, (Apr. 25, 2008), 17 pgs.

Sukumaran, R. K, et al., "Cellulase production using biomass feed stock and its application in lignocellulose saccharification for bioethanol production", Renewable Energy, 34(2), (Feb. 2009), 421-424.

Sulbaran-De-Ferrer, B., et al., "Enzymatic hydrolysis of ammonia-treated rice straw", Appl Biochem Biotechnol., 105-108, (Spring, 2003), 155-64.

Sun, Y., et al., "Hydrolysis of Lignocellulosic materials for ethanol Production", Bioresource Rechnology, 83, (2002), 1-11.

Suto, M., et al., "Induction and catabolite repression mechanisms of cellulase in fungi", Journal of Bioscience and Bioengineering, 92, (2001), 305-311.

Teymouri, F., et al., "Optimization of the ammonia fiber explosion (AFEX) treatment parameters for enzymatic hydrolysis of corn stover", Bioresour Technol., 96(18), (Dec. 2005), 2014-18.

Uraki, Y, et al., "Boday temperature-responsive gels derived of hydroxypropylcellose bearing lignin II: Adsorption and release behavior", Cellulose, 13, (2006), 225-234.

Urribarri, Lauris, et al., "Leaf Protein from Ammonia-Treated Dwarf Elephant Grass (*Pennisetum purpureum* Schum cv Mott)", Appl. Biochem. and Biotechnol. vol. 121-124, (2005), 721-730.

Waiss, Jr, A. C, et al., "Improving Digestibility of Straws for Ruminant Feed by Aqueous Ammonia", Journal of Animal Science; 35(1), (1972), 109-112.

Ye, D, et al., "Improving accessibility and reactivity of cellulose of annual plants for the synthesis of methylcellulose", Cellulose, 12, (2005), 507-515.

Zhang, Y H, et al., "A transition from cellulose swelling to cellulose dissolution by o-phosphoric acid: evidence from enzymatic hydrolysis and supramolecular structure", Biomacromolecules, 7(2), (Feb. 2006), 644-8.

Zhang, Y-H. P, et al., "Toward an Aggregated Understanding of Enzymatic Hydrolysis of Cellulose: NonComplexed Cellulase Systems", Biotechnol. Bioeng., 88, (2004), 797-824.

Zhou, S., et al., "Gene integration and expression and extracellular secretion of *Erwinia chrysanthemi* endoglucanase CelY (celY) and CelZ (celZ) in ethanologenic *Klebsiella oxytoca* P2", Appl. Environ. Microbiol., 67(1), (2001), 6-14.

U.S. Renewable Fuels Association website—Fuel Ethanol Industry Bio-Refineries and Production Capacity, dated Mar. 27, 2007.

Bothast, R.J. and Schlicher, M.A., Biotechnological processes for conversion of corn into ethanol, Appl. Microbiol Biotechnol., 67: 19-25 (2005).

Hahn-Hägerdal B, Galbe M, Gorwa-Grauslund MF, Lidén G, and Zacchi G, Bio-ethanol—the fuel of tomorrow from the residues of today, Trends in Biotech., vol. 24, No. 12, p. 549-556 (2006).

Gray KA, Zhao L, and Emptage M, Bioethanol. Current Opinion in Chemical Biology 10:141-146 (2006).

Wheals AE, Basso LC, Alves DMG and Amorim HV, Fuel ethanol after 25 years, TIBTECH, 17:482-487 (1999).

Mosier N, Wyman C, Dale B, Elander R, Lee YY, Features of promising technologies for pretreatment of lignocellulosic biomass, Bioresource Technol. 96, 673-686 (2005).

Rajagopalan S, Ponnampalam, McCalla D and Stowers M, Enhancing Profitability of Dry Mill Ethanol Plants, Appl. Biochem. Biotechnol, 120, 37-50 (2004).

Rausch KD and Belyea RL, The future of co-products from corn processing. Appl. Biochem. Biotechnol. 128, 47-86 (2006).

Belyea RL, Clevenger TE, Shingh V, Tumbleson ME and Rausch KD, Element Concentrations of Dry-Grind Corn-Processing streams, Appl. Biochem. Biotechnol. 134, 113-128 (2006).

U.S. Appl. No. 11/729,632—"Process for Conversion of Mushroom Lignocellulose Waste to Useful Byproducts"; Supplemental Response to Office Action flied Oct. 30, 2009.

U.S. Appl. No. 11/729,632—"Process for Conversion of Mushroom Lignocellulose Waste to Useful Byproducts"; Non-Final Office Action mailed May 6, 2009.

U.S. Appl. No. 11/729,632—"Process for Conversion of Mushroom Lignocellulose Waste to Useful Byproducts"; Response to Non-Final Office Action filed Sep. 11, 2009.

U.S. Appl. No. 11/897,119—"Production of Microbial Growth Stimulant with Ammonia Fiber Explosion (AFEX) Pretreatment and Cellulose Hydrolysis"; Restriction Requirement mailed Sep. 30, 2011.

U.S. Appl. No. 12/229,225—"Process for Pretreating Plant Biomass"; Response to Non-Final Office Action filed Nov. 15, 2011.

U.S. Appl. No. 12/229,226—"Process for Pretreatment Plant Biomass"; Non-Final Office Action mailed Aug. 16, 2011.

U.S. Appl. No. 12/226,763—"Process for Treatmen tof Lignocellulose Biomass": Non-Final Office Action mailed Aug. 22, 2011.

Chang, Shu-Ting, "The World Mushroom Industry; Trends and Technological Development", International Journal of Medicinal Mushrooms, vol. 8, pp. 297-314; 2006.

de Ferrer, et al, "NR 06. Sugar Production From Rice Straw", Arch. Latinoam Prod. Anim., 5(Supl. 1), pp. 112-114; 1997.

Chahal, D,S., "Bioconversion of Hemicelluloses into Useful Products in an Integrated Process for Food/Feed and Fuel (Ethanol) Production from Biomass", Biotechnology and Bioengineering Symp. No. 14, pp. 425-433; 1984.

U.S. Appl. No. 12/226,763, Response filed Dec. 21, 2011 to Non Final Office Action mailed Aug. 22, 2011, 11 pgs.

U.S. Appl. No. 12/226,763, Final Office Action mailed Jan. 10, 2012, 16 pgs.

U.S. Appl. No. 12/976,344, Notice of Allowance mailed Feb. 23, 2012, 7 pgs.

U.S. Appl. No. 11/729,632, Notice of Allowance mailed Nov. 16, 2009, 7 pgs.

U.S. Appl. No. 12/229,225, Response filed Nov. 15, 2011 to Non Final Office Action mailed Aug. 16, 2011, 12 pgs.

U.S. Appl. No. 12/976,344, Notice of Allowance mailed Mar. 27, 2012, 8 pgs.

Adaoa, P. et al., "Compression Characteristics of Selected Ground Agricultural Biomass", Agricultural Engineering International: The CIGR Ejournal, Manuscript 1347, vol. XI, (Jun. 2009), 19 pgs.

Miller, Norman, "Re: Commitment Letter "Phase I Biomass Enhanced Refined Lignite Demonstration Project"", http://www.nd.gov/ndic/renew/meeting0903/r005-a-prop.pdf,(Dec 2008),24 pgs.

Mosier, Nathan "Features of Promising Technologies for Pretreatment of Lignocellulosic Biomass", Bioresource Technology, vol. 96, No. 6, (Apr. 2005),673-686.

Teymouri, Farzaneh et al., "Optimization of the Ammonia Fiber Explosion (AFEX) Treatment Parameters for Enzymatic Hydrolysis of Corn Stover", Bioresource Technology, vol. 96, (2005), 2014-2018.

* cited by examiner

PROCESS FOR PRODUCING SUGARS AND ETHANOL USING CORN STILLAGE

CROSS REFERENCE TO RELATED APPLICATIONS

Priority to U.S. Provisional Application Ser. No. 60/997,458, filed Oct. 3, 2007, which is incorporated herein by reference in its entirety, is claimed.

BACKGROUND OF THE DISCLOSURE

1. Field of the Disclosure

The present disclosure relates to a process for the treatment of a lignocellulosic material with the addition of corn stillage to produce sugars and/or ethanol fermented therefrom. The process can incorporate an ammonia fiber explosion (AFEX) process to disrupt the lignocellulosic material. The biomass is treated with enzymes to produce the sugars.

2. Brief Description of Related Technology

In the United States, ethanol is primarily made from corn starch.[1] There are two major industrial processes producing ethanol: wet milling and dry milling. In both processes, the extracted starch is cooked, liquified, saccharified by a mixture of enzymes (α-amylase and glucoamylase) and fermented to beer.[2-5] The beer is passed through a distillation system to separate ethanol from water and other soluble solids, referred to as distiller's solubles (DS). During this process, a large amount of distiller's solubles is generated, also called "thin stillage." In order to sell wet distillers grain (WDG) as useful byproducts, the stillage is concentrated and mixed with wet distillers grain, dried and marketed as distillers dried grains (DDG). Removal of water from corn-processing streams is costly in terms of energy (700-3000 kJ/kg of water, i.e., about 30% energy requirements of the entire plant) and involves the use of equipment that contributes to capital and operating expenses.[1]

Ethanol processes face some difficult challenges if they are to improve competitiveness, profitability and sustainability while reducing co-product variability and energy costs. The nascence of the first generation corn stover lignocellulosic biorefinery will be through an existing dry or wet mill corn based ethanol industry. However, a commercially successful biorefinery will only come into existence through further reduction in processing costs.

Most of the current ethanol produced in the United States uses feed corn as a feedstock. Corn is the most important and economical source of starch in the United States. Starch is the major carbohydrate storage product in corn kernels comprising 70-72% of the kernel weight on a dry weight basis. Starch is readily converted to glucose using α-amylase and glucoamylase enzymes and fermented into ethanol using yeast. Today, most fuel ethanol is produced from corn by either the dry grind (67%) or the wet mill (33%) process. The key distinction between wet mill and dry grind facilities is the amount of water used in the process. Current technologies allow for 2.5 gallons (wet mill) to 2.8 gallons (dry grind) of ethanol per bushel of corn.

The wet milling process is more capital- and energy-intensive, as the grain must first be separated into its components, including starch, fiber, gluten, and germ. The germ is removed from the kernel and corn oil is extracted from the germ. The remaining germ meal is added to fiber and the hull to form corn gluten feed. Gluten is also separated to become corn gluten meal, a high-protein animal feed. The starch solution is separated from the solids and fermentable sugars are produced from the starch. These sugars are fermented to ethanol. The wet mill produces a number of high-value products. About 1.6 pounds of corn oil, 2.6 pounds of gluten meal, and 13.5 pounds of gluten feed are generated via this process per bushel of corn In the dry grind process, the clean corn is ground and mixed with water to form a mash. The mash is cooked and enzymes are added to convert starch to sugar. Then yeast is added to ferment the sugars, producing a mixture containing ethanol and solids. This mixture is then distilled and dehydrated to create fuel-grade ethanol. The solids remaining after distillation are further dried to produce distillers' dried grains with protein and are sold as an animal feed supplement. For every bushel of corn, 17 pounds of DDGS are generated by this process.

In the dry grind process, the solid and liquid fractions remaining after distillation are referred to as "whole stillage." Whole stillage includes the fiber, oil, and protein components of the grain, as well as the non-fermented starch. This co-product is a valuable feed ingredient for livestock, poultry, and fish. Although it is possible to feed whole stillage, it is usually dried further before being sold as feed to prevent microbial contamination. First, the "thin stillage" is separated from the insoluble solid fraction using centrifuges or presses/extruders. The stillage leaving the beer column is centrifuged with a decanter. Between 15% and 30% of the liquid fraction (thin stillage) is recycled as backset. The remainder is concentrated further by evaporation and mixed with the residual solids from the fermentation. After evaporation, the thick, viscous syrup is mixed back with the solids to create a feed product known as wet distiller's grains with soluble (WDGS). WDGS, containing 65% moisture, can be used directly as a feed product. In fact, it is often favored by dairy and beef feeders because cattle seem to prefer the moist texture. However, WDGS has a shelf-life of only 1-2 weeks. Unless the feedlot is within about 50 miles (80 km) of the ethanol plant, handling and storage can be a challenge, especially in hot summer months when shelf-life is very limited. To increase shelf-life and reduce transportation costs, WDGS is usually dried to about 10-12% moisture, to produce DDGS. Drying WDGS is energy-intensive, consuming about one-third of the energy requirements of the entire dry grind plant. However, producing a uniform, stable, high-quality feed co-product is essential to the profitability of the plant, resulting in most plants producing DDGS rather than WDGS. Currently, dry grind ethanol plants produce over $5.5 \times 10^6$ tons of DDGS per year, and the amount is increasing.

Objects

It is an object to minimize energy spent during conventional corn ethanol processes using corn stillage to reduce the processing cost and to optimize the utilization of water resources in combination with other processes. It is further an object to increase the glucan yield of from lignocellulosic material using the corn stillage, thereby also increasing the yield of a subsequent ethanol fermentation process.

These and other objects may become increasing apparent by reference to the following description and the drawings.

SUMMARY

In the present disclosure, sugars are produced from a lignocellulosic material by enzymatic hydrolysis of complex carbohydrates in the lignocellulosic material. The sugar yield is increased by adding corn grain stillage (which contains corn protein) to the lignocellulosic material prior to the enzymatic hydrolysis. Ethanol can be subsequently formed by yeast fermentation of the sugars.

In the United States, there are about 114 existing dry/wet mills (total current capacity: 5633 million gallons per year (mgy)) and 80 (6394 mgy) new mills coming up to produce ethanol from corn grain through biomass hydrolysis and fermentation (FIG. 1). Individual biorefineries ranging from small- to large-scale plants produce ethanol at capacities ranging from 3 mgy to 115 mgy. Dry mill corn ethanol processing shows a large quantity of waste stream (thin stillage) generation. About 15-30% of stillage is used for recycling and remaining 70-85% are further concentrated by evaporation and mixed with wet distillers grain (WDG), followed by drying and sold as DDG (as animal feed) in the market. At present, the stillage concentration process and drying WDG alone consumes 30% of total plant energy.

The disclosed processes, however, utilize these corn stillage waste streams from existing corn ethanol facilities. The corn stillage (which contains about 2% soluble proteins) can be used as an additive (e.g., as a liquid stream) to an enzymatic hydrolysis process for lignocellulosic material. For this purpose, the stillage can be used in its different forms: either the whole stillage or the products of its centrifugation (e.g., thin stillage and/or wet distiller's grain). The lignocellulosic material can be pretreated, for example by performing an ammonia fiber explosion (AFEX) process. The benefits of using the corn stillage as an additive include: (1) saving water resources, (2) reducing energy costs by 30% (e.g., associated with heating, drying), (3) improving the hydrolysis yield and rate of the lignocellulosic material, for example due to presence of protein in corn stillage, and (4) improvements in other downstream processes (e.g., ethanol fermentation, where the protein and other stillage components can be used as a rich nutrient source by microbes). In addition to these benefits, by adding thin stillage to corn stover hydrolysis, it was found that there was about a 5-20% improvement in sugar hydrolysis yield as compared to adding pure water (FIG. 3), thus greatly improving the economics of corn processing into ethanol. The processes also allow the synergistic unification of existing corn-starch ethanol industries with lignocellulosic biorefineries (e.g., which use corn stover as a feedstock, thus enabling the bioconversion of substantially the whole corn plant (i.e., corn grain and corn stover)). Such synergism can increase revenues and reduce the maximum selling price (MSP) of ethanol in existing corn-starch ethanol facilities.

In an embodiment, a process for producing sugars from a lignocellulosic material comprises: (a) adding corn grain stillage to the lignocellulosic material; (b) treating the lignocellulosic material with one or more hydrolyzing enzymes (e.g., one or more cellulases and, optionally, one or more hemicellulases), thereby hydrolyzing complex carbohydrates in the lignocellulosic material and forming the sugars; and then optionally (c) fermenting the sugars (e.g., in the same or different vessel as the hydrolysis; for example to form ethanol). The corn grain stillage can comprise whole grain stillage with solids and/or thin stillage. Preferably, step (a) further comprises: (a-1) separating the corn grain stillage into a thin stillage component and a wet grain component; (a-2) drying the wet grain, thereby forming distillers dried grains with solubles (DDGS); and (a-3) adding the thin stillage and the DDGS to the lignocellulosic material. Preferably, the corn grain stillage comprises about 0.05 wt. % to about 50 wt. % crude corn protein (e.g., about 0.1% to about 10%, about 0.5% to about 5%, about 1% to about 4%, or about 2%). The lignocellulosic material can comprise one or more of corn stover, miscanthus, rice straw, poplar, and bagasse. Preferably, the lignocellulosic material is pretreated prior to treating the lignocellulosic material with the hydrolyzing enzymes, thereby disrupting the lignocellulosic material. Suitable pretreatment processes include one or more of an ammonia fiber explosion (AFEX) process, a dilute-acid treatment process, a dilute-base treatment process, an ammonia recycle percolation process, a steam explosion process, a high-temperature exposure process, an irradiation process, a lime pretreatment process, an alkaline wet oxidation process, and an ionic liquid pretreatment process.

In a refinement of any of the foregoing processes, the lignocellulosic material is treated in an aqueous medium comprising the lignocellulosic material, the corn grain stillage, the hydrolyzing enzymes, and optionally additional water. Preferably, the aqueous medium has a glucan loading (i.e., as a component of the lignocellulosic material) of lignocellulosic material ranging from about 0.1 wt. % to about 20 wt. % (e.g., up to about 4%, about 1% to about 4%, about 4% to about 15%, or about 9% to about 12%). Additionally, the aqueous medium can comprise about 0.5 wt. % to about 99 wt. % corn grain stillage relative to the aqueous medium (e.g., at least about 10%, at least about 40%, about 10% to about 90%, about 25% to about 70%). Further, the aqueous medium comprises about 0.02 wt. % to about 5 wt. % crude corn protein (i.e., as a component of the corn grain stillage) relative to the aqueous medium (e.g., about 0.05% to about 4%, about 0.1% to about 3%, about 0.2% to about 2%, about 0.3% to about 1.5%).

In another embodiment, a process for producing sugars from corn stover comprises: (a) pretreating the corn stover with an ammonia fiber explosion (AFEX) process, thereby disrupting the corn stover; (b) adding thin corn grain stillage to an aqueous medium comprising the pretreated corn stover; (c) treating the corn stover in the aqueous medium with one or more cellulase enzymes, thereby hydrolyzing cellulose in the corn stover and forming the sugars; and then optionally (d) fermenting the sugars (e.g., to form ethanol). In one refinement, the aqueous medium has a corn stover glucan loading ranging from about 1 wt. % to about 4 wt. %. In another refinement, the aqueous medium has a corn stover glucan loading ranging from about 4 wt. % to about 15 wt. %.

In another embodiment, an improvement in a corn grain-ethanol production process is disclosed. Specifically, in a process for producing ethanol from corn grain in which dry-ground or wet-milled corn grain is (1) enzymatically treated to convert corn grain starches to sugars, (2) fermented with yeast to convert the sugars to ethanol, and (3) distilled to recover the ethanol, thereby producing solid and liquid bottoms fractions as a corn stillage by-product, the improvement comprises: (a) adding the corn stillage from the corn grain processing to a lignocellulosic material. Preferably, the process further comprises: (b) treating the combination of the corn stillage and the corn stover from step (a) with one or more cellulase enzymes, thereby hydrolyzing cellulose in the corn stover and forming sugars. In another refinement, the process further comprises: (c) fermenting the sugars, thereby forming ethanol; and (d) recycling the fermented ethanol for distillation and recovery of the ethanol.

All patents, patent applications, government publications, government regulations, and literature references cited in this specification are hereby incorporated herein by reference in their entirety. In case of conflict, the present description, including definitions, will control.

Also related are Provisional Application No. 60/936,509, filed Jun. 20, 2007; PCT Application Nos. PCT/US07/10410, filed Apr. 30, 2007 (WO 2008/020901) and PCT/US07/10415, filed Apr. 30, 2007 (WO 2007/130337); U.S. application Ser. No. 11/729,632, filed Mar. 29, 2007; U.S. application Ser. No. 11/901,336, filed Sep. 17, 2007; Dale et al. U.S. patent application entitled "Process for Enzymatically Converting a Plant Biomass" and filed Aug. 8, 2008; U.S. Pat. Nos. 6,106,888 to Dale et al. and 6,176,176 to Dale et al., which are incorporated herein by reference in their entireties, in particular in regard to various lignocellulosic pretreatment and ethanol production processes.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein:

FIG. 2-1 illustrates a conventional corn ethanol process 105 for integration with the process of FIG. 2 in which whole stillage is processed and dried to dry distillers grains with solubles (DDGS), in addition to producing ethanol.

FIG. 2-2 illustrates an embodiment of the disclosed process 200 in which the lignocellulosic material is pretreated and the thin stillage is added prior to enzymatic hydrolysis, and in which dried distillers grain with solubles (DDGS) is produced as a secondary product by drying wet distillers grain (WDG).

FIG. 2-3 illustrates an alternative process 300 to the embodiment of FIG. 2-2 in which the DDGS (dried to an appropriate moisture level) is hydrolyzed and fermented to ethanol as an additional cellulosic feed stock.

FIG. 3 is a flow chart illustrating steps according to the disclosed processes.

Figure 1:
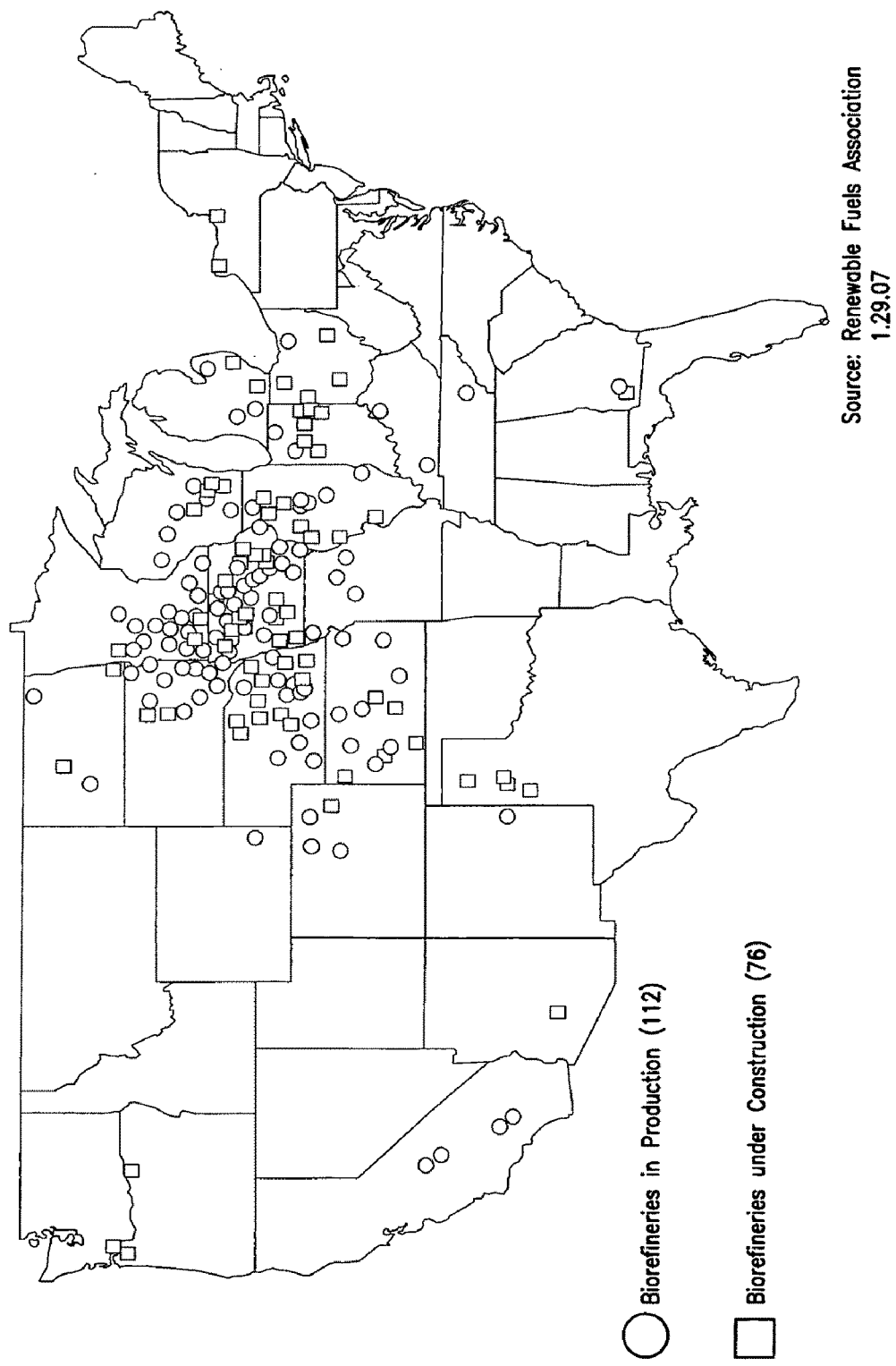
FIG. 1 is a map illustrating the location of corn ethanol biorefineries in the United States.

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

Processes according to the disclosure are suitable for producing sugars from a lignocellulosic material. The process generally includes a step of adding corn grain stillage to the lignocellulosic material. The lignocellulosic material is then treated (i.e., in combination with the stillage) with one or more hydrolyzing enzymes. The enzymes hydrolyze the complex carbohydrates in the lignocellulosic material to form the sugars (e.g., simple sugars such as glucose) that can be further fermented to form ethanol.

The corn grain stillage can be formed as a by-product of corn ethanol production (e.g., dry grind or wet mill). A suitable dry-mill corn ethanol process 100 is illustrated in FIG. 2 (process diagram for a conventional dry mill corn ethanol plant) and FIG. 3 (flow chart for steps according to the disclosed processes). Corn grain 112 is milled in a hammer mill 110 and formed into a slurry in a slurry tank 120. The resulting mash is cooked in a jet cooker 130, liquified/saccharified in a liquefaction vessel 140 with the addition of enzymes 142 (e.g., amylases such as α-amylase and glucoamylase), and the cooled in a cooler 150. The mash is then fermented in a fermentation vessel 160 with the addition of yeast 162, and the resulting ethanol-containing beer stream is purified in a distillation system 170. The distillate product of the distillation system 170 is about 190 proof ethanol E1 that is further purified to about 200 proof with molecular sieves 180. The bottoms product of the distillation system 170 is the corn grain stillage. Stillage streams S1, S2, and S3 represent the inlet streams to the processes illustrated in FIGS. 2-1 to 2-3, respectively. Beer streams B2 and B3 represent the return, ethanol-containing beer streams from FIGS. 2-2 and 2-3, respectively, both of which can be recycled to the distillation system 170 for purification and recovery of the ethanol.

The corn grain stillage (or simply "stillage") exiting the distillation system 170 is a "whole stillage" that is generally an aqueous mixture including components such as the fiber, oil, and protein (e.g., crude corn protein) components of the grain, as well as the non-fermented starch. Some of the components are water-soluble, and some components are insoluble suspended solids. As an additive to the lignocellulosic material, the stillage can be used in the form that it exits the distillation system 170, or only a portion/component of the stillage can be used. Preferably, the stillage is separated (e.g., by centrifugation, pressing, extrusion) into a substantially liquid fraction (i.e., thin stillage, for example still containing about 10 wt. % or less solids, or about 1 wt. % to about 6 wt. % solids) and a substantially solid fraction (i.e., wet distillers grain). Additionally, the stillage can include the liquid fraction of the thin stillage (e.g., "liquid thin stillage" representing thin stillage that has additionally processed to remove substantially all of the residual solids from the thin stillage). Table 1 in Example 1 presents the compositional analysis of thin stillage in its various forms. The crude protein content of the stillage can vary according to the particular type of stillage used. Preferably, the stillage includes about 0.05 wt. % to about 50 wt. % crude corn protein, for example about 0.1 wt. % to about 10 wt. %, about 0.2 wt. % to about 2 wt. %, about 0.5 wt. % to about 5 wt. %, about 0.5 wt. % to about 1 wt. %, about 1 wt. % to about 4 wt. %, or about 2 wt. %.

Figure 2:
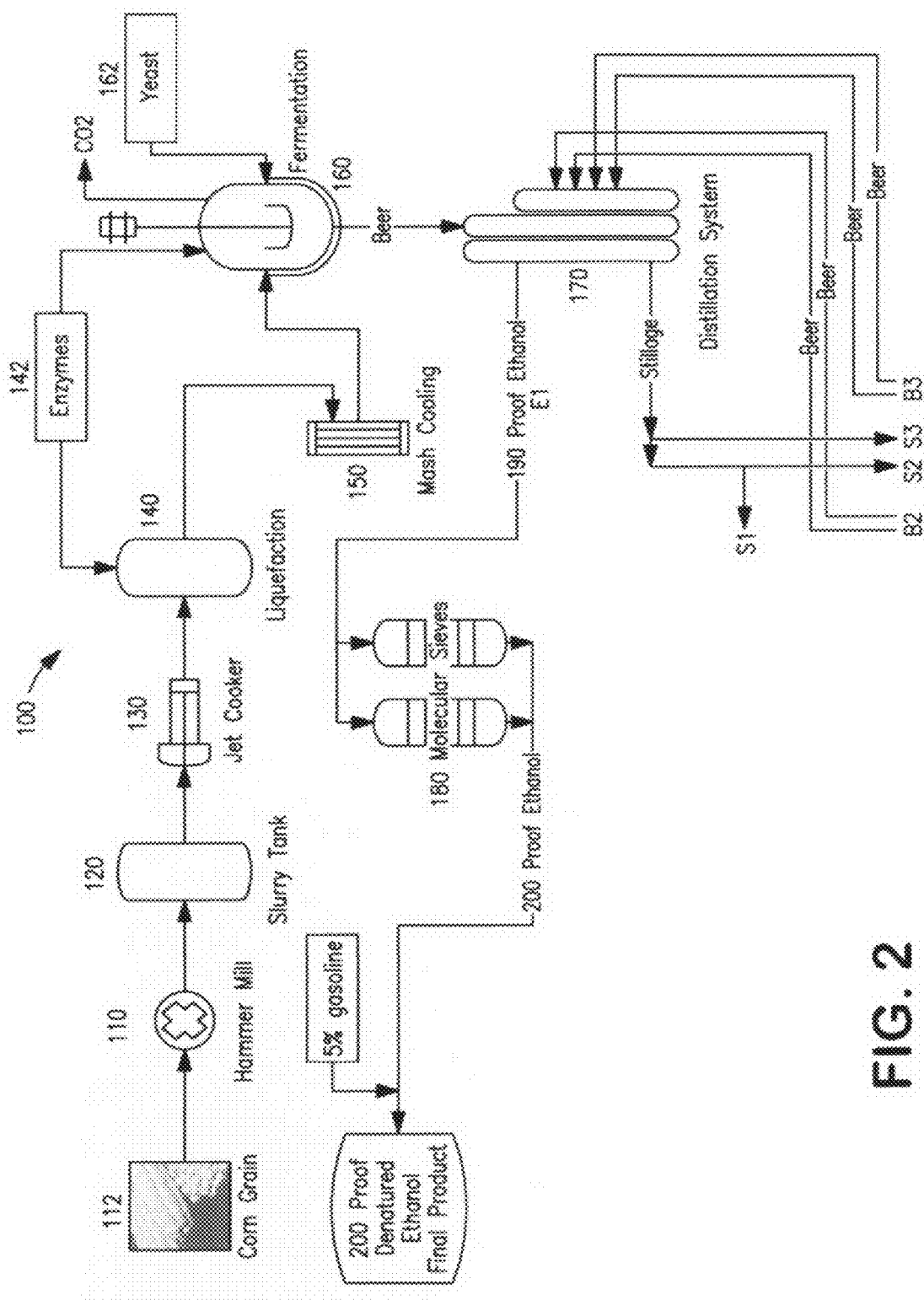
FIG. 2 is a process diagram illustrating the components of a conventional dry mill corn ethanol plant process 100.
Figures 1, 2:
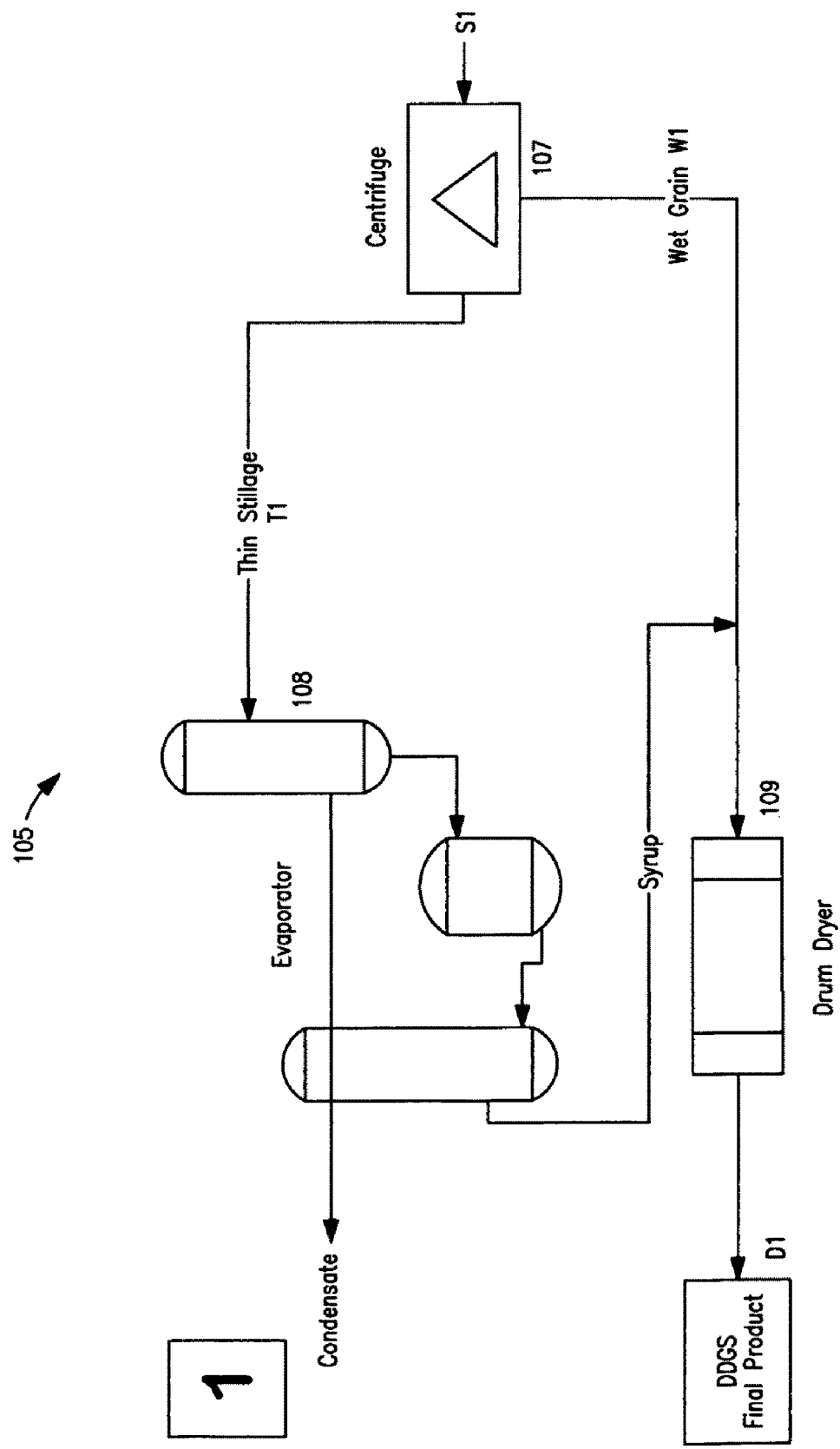
Figure 2:
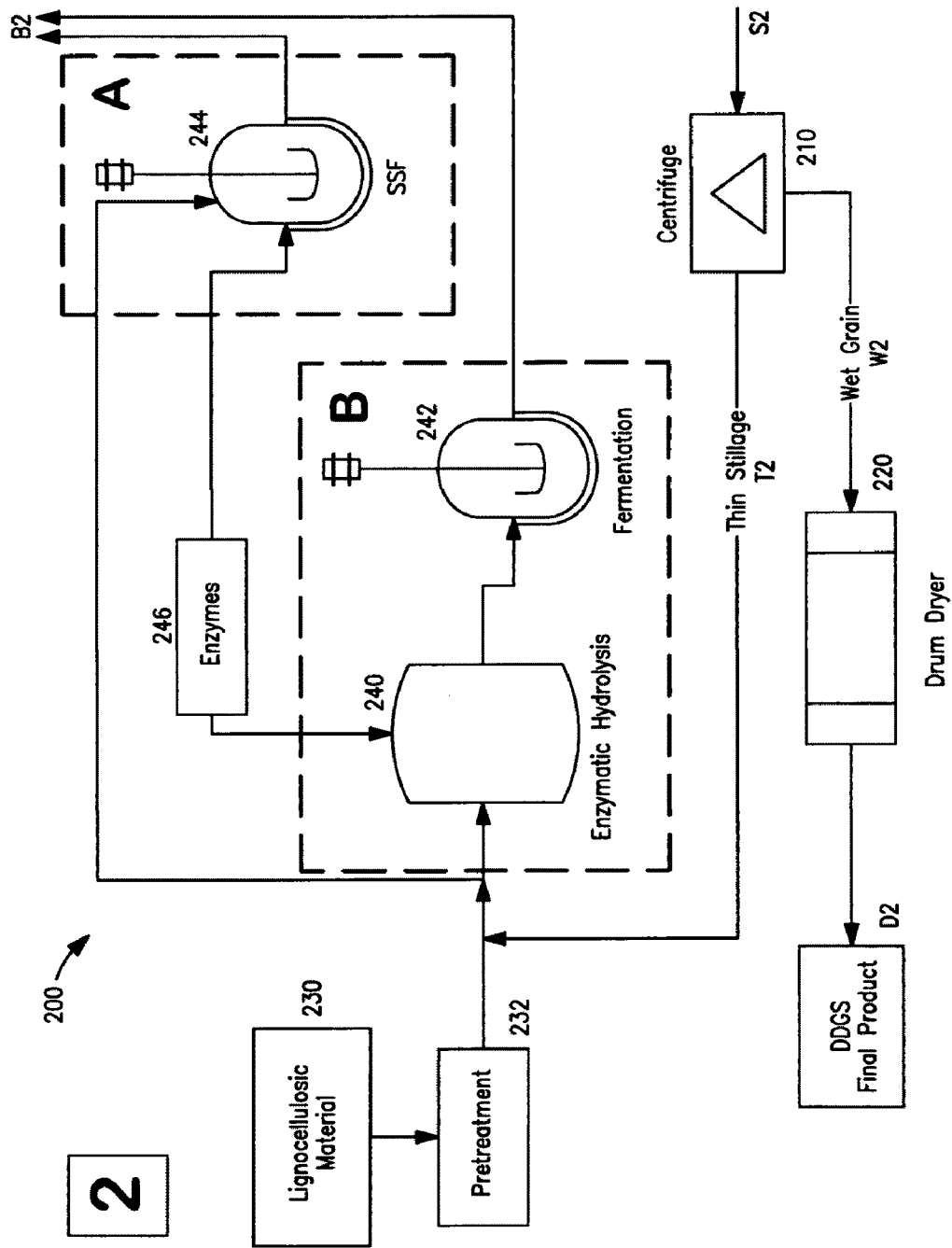

FIG. 2-1 illustrates the remainder of a conventional corn ethanol process 105. The stillage stream S1 is fed to a centrifuge 107 to create a thin stillage fraction T1 and a wet distillers grain fraction W1. The thin stillage T1 water content is reduced in an evaporator 108 and the wet distillers grain W1 is dried in a dryer 109 to create a DDGS product stream D1.

Figures 2, 3:
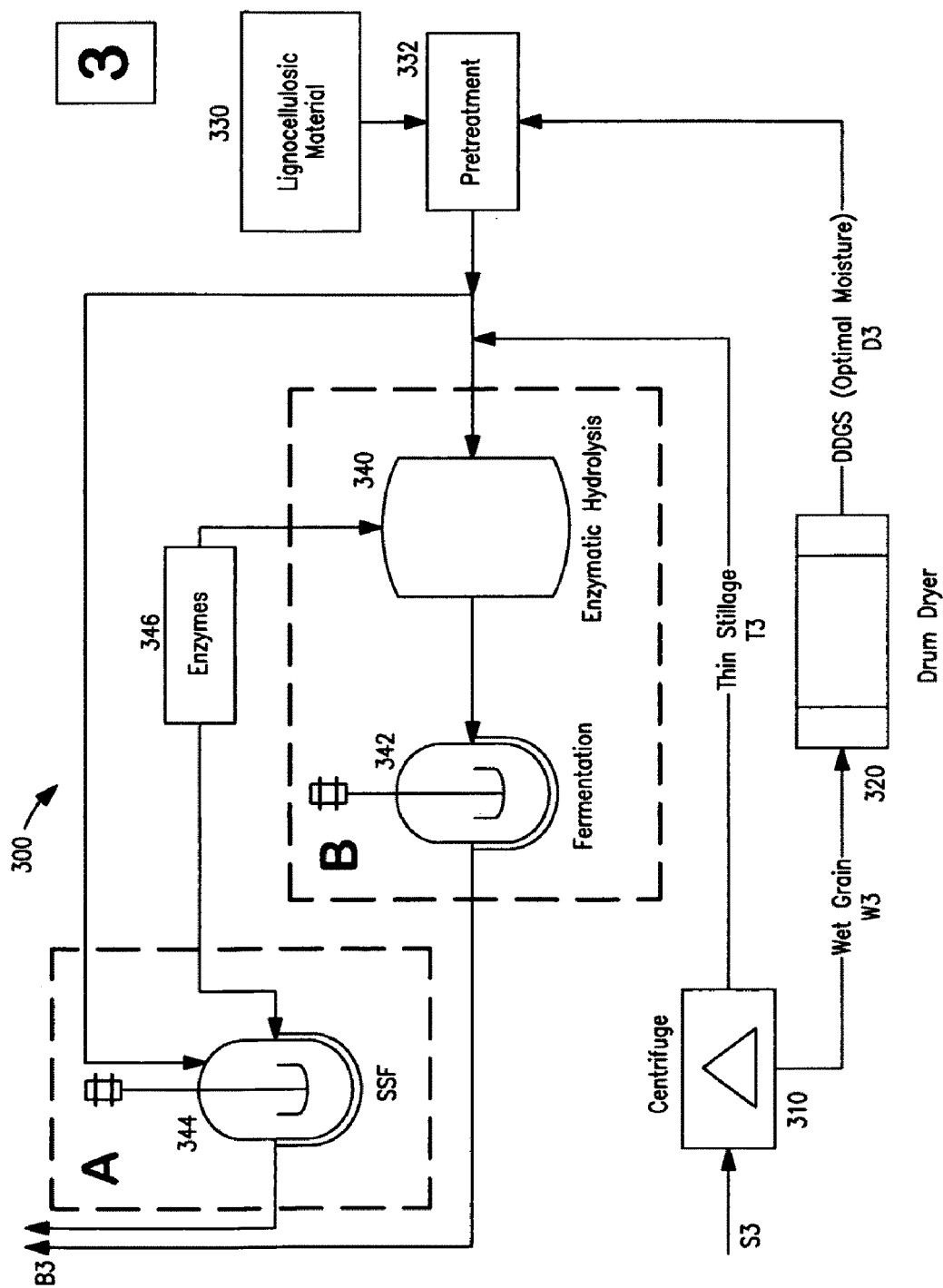
Figure 3:
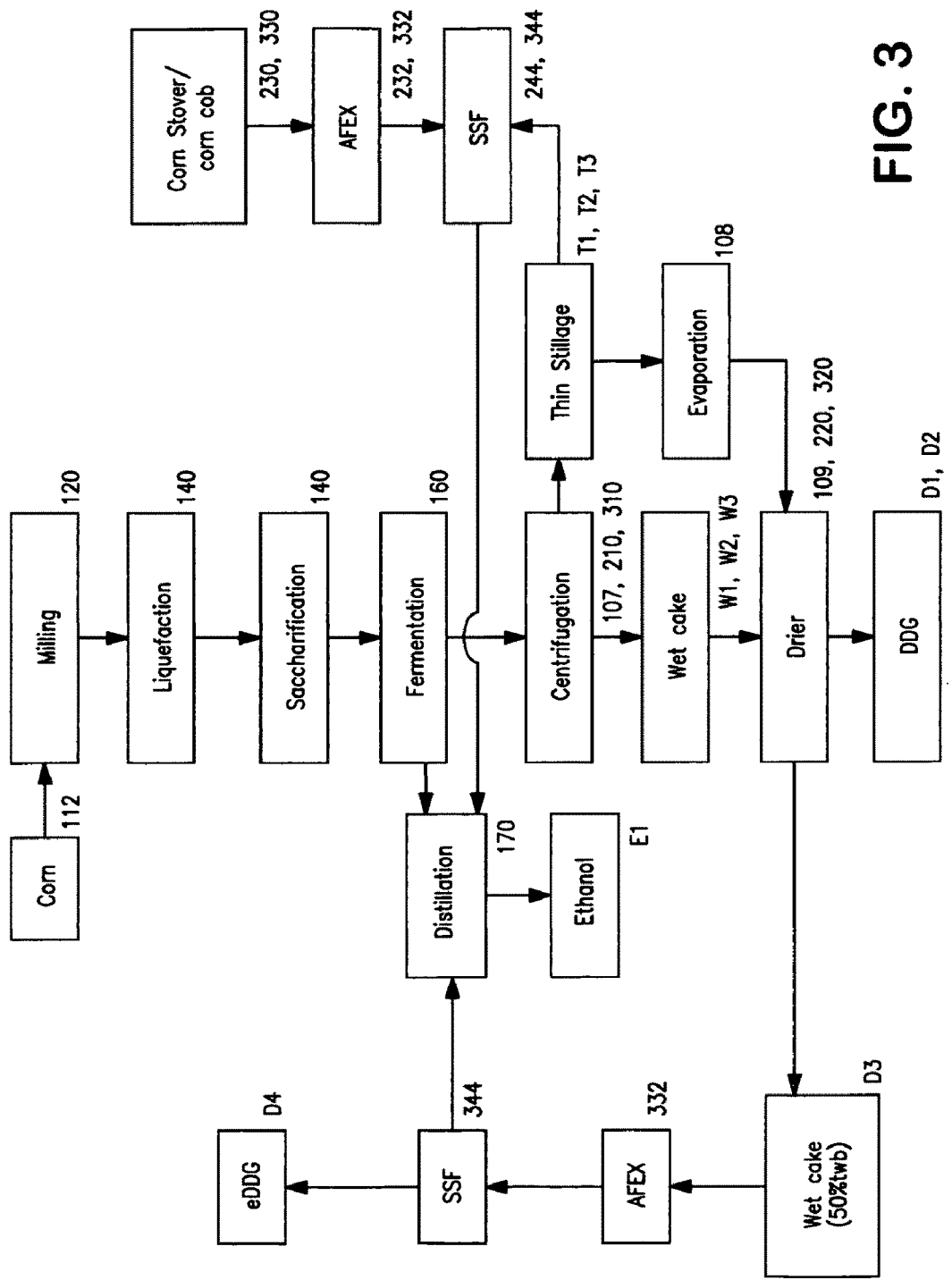

FIGS. 2-2 and 2-3 illustrate processes 200 and 300 according to the disclosure. Both processes 200 and 300 can be integrated into a corn ethanol process, for example as illustrated in FIG. 3. In FIG. 2-2, lignocellulosic pretreatment facilities are installed in existing corn ethanol plants, followed by utilization of stillage (liquid with fine particles) generated in a corn ethanol plant as a liquid stream for lignocellulosic hydrolysis and fermentation, further followed by mixed sugar ethanol fermentation using either native or engineered microbes. The wet distillers grains are dried and can be sold as DDGS in the market for animal feed. In FIG. 2-3, the wet distillers grains are dried to optimal moisture and pretreated using one of the pretreatment technologies followed by hydrolysis, and mixed sugar fermentation to ethanol. Here again, the thin stillage is used for the hydrolysis and subsequent fermentation process. As illustrated specifically in FIGS. 2-2 and 2-3, whole stillage streams S2, S3 are fed to a separator (e.g., centrifuge 210, 310) to create a thin stillage fraction T2, T3 and a wet distillers grain fraction W2, W3. The thin stillage T2, T3 is then combined with lignocellulosic material 230, 330 that has been pretreated 232, 332 (e.g., in an AFEX process) prior to enzymatic hydrolysis. The wet distillers grain is dried in a drum dryer 220, 320 to form DDGS (e.g., about 10-12 wt. % moisture). In the process 200, the DDGS stream D2 is recovered as a final product (e.g., as animal feed). In the process 300, the DDGS stream D3 at optimal moisture (e.g., about 10-70 wt. % on a wet-weight basis or about 10-250 wt. % on a dry-weight basis) is used as a co-feed with the lignocellulosic material 330 that can be similarly pretreated (e.g., with an AFEX or other pretreatment process 332) prior to hydrolysis. In either process 200 or 300, two options are available: (a) simultaneous saccharification and fermentation (SSF) or (b) separate hydrolysis and fermentation (SHF). Specifically, the lignocellulosic material and stillage can be enzymatically hydrolyzed with enzymes 246, 346 in a hydrolysis vessel 240, 340 and then fermented with yeast in a fermentation vessel 242, 342. Alternatively, the lignocellulosic material and stillage can be both enzymatically hydrolyzed and fermented in the same vessel 244, 344. When the DDGS stream D3 is used as a co-feed with the lignocellulosic material 330, the process additionally produces an enhanced DDG (eDDG) stream D4 as a product of hydrolysis/fermentation. Because fibrous and other cellulosic material has been removed, the eDDG has an enhanced protein content (e.g., at least about 50 wt. %, about 50 wt. % to about 90 wt. %, or about 70 wt. %) as compared to normal DDG/DDGS (e.g., about 25 wt. %). The ethanol distillation and purification in either process 200 or 300 is similar to the existing corn ethanol processes and hence, the existing facilities can be expanded to suit the needs.

Although both FIGS. 2-2 and 2-3 illustrate the fermentation of hydrolyzed sugars to form ethanol, fermentation is an optional process step, inasmuch as the hydrolyzed sugars can be separated and recovered as a final product. Further, fermentation processes for chemicals other than ethanol can be performed on the hydrolyzed sugars. For example, selection of a suitable fermentation organism can be used to convert the hydrolyzed sugars to alcohols (e.g., methanol, ethanol, propanol, butanol, or other alkyl alcohols), organic acids (e.g., lactic acid), and/or proteins.

The lignocellulosic material suitable for use in the disclosed processes is not particularly limited, and generally includes plant material or "biomass" that contains a substantial amount of complex carbohydrates (e.g., cellulose, hemicellulose) and lignin. Other components can include, depending on the particular lignocellulosic material, starch, simple sugars, protein, lipids, pectin, minerals and a host of minor components. Cellulose is a structural component of the lignocellulosic material and is a crystalline $\beta(1\rightarrow4)$ glycosidic polysaccharide. Hemicellulose is also a structural component of the lignocellulosic material, and is generally an amorphous polysaccharide of multiple sugar monomers including glucose, xylose, mannose, galactose, rhamnose, and arabinose. Suitably, the lignocellulosic material contains at least about 10 wt. % cellulose (e.g., at least about 20 wt. %, at least about 30 wt. %). Similarly, the lignocellulosic material generally contains about 60 wt. % or less cellulose (e.g., about 50 wt. % or less, about 40 wt. % or less). Suitable examples of lignocellulosic materials include corn stover, high-energy grasses (e.g., miscanthus), straws (e.g., rice, wheat, barley, oat, rye), poplar, and bagasse. For example, corn stover generally contains about 30 wt. %-40 wt. % cellulose, about 15 wt. %-30 wt. % hemicellulose, and about 10 wt. %-20 wt. % lignin. The lignocellulosic material is preferably milled or otherwise comminuted by any conventional means (e.g., to a particle size ranging from about 100 µm to about 1000 µm, for example as specified in the NREL LAP protocol, NREL Technical Report NREL/TP-510-42620, incorporated herein by reference).

The lignocellulosic material is then treated (i.e., in combination with the stillage supplement) with one or more hydrolyzing enzymes. Preferably, the treatment is performed in an aqueous medium containing the lignocellulosic material, the corn grain stillage, the hydrolyzing enzymes, and (in some cases) water. The aqueous hydrolysis medium can have any suitable glucan loading from the lignocellulosic materials, for example ranging from about 0.1 wt. % to about 20 wt. % based on the total weight of the medium. In low-solids applications, the glucan loading can be about 4 wt. % or less, for example about 1 wt. % to about 4 wt. %. In high-solids application where the benefits of adding stillage can be more pronounced (e.g., due to enzyme inhibition effects that would otherwise limit glucan conversion at high loading levels), the glucan loading preferably ranges from about 4 wt. % to about 15 wt. % or about 9 wt. % to about 12 wt. %. The glucan content of lignocellulosic material refers to the glucose monomeric portion of the lignocellulosic polysaccharides (e.g., cellulose) which, if completely hydrolyzed, could be recovered as glucose monosaccharide sugars. The glucan loading of the aqueous medium can be equivalently expressed in terms of a total solids loading of lignocellulosic material based on the glucan content of the lignocellulosic material. Corn stover, for example, contains about ⅓ glucan, so an aqueous medium having a glucan loading of about 6 wt. % has a solids loading of about 18 wt. %, with the additional 12 wt. % representing non-glucan components of the lignocellulosic material. Suitable lignocellulosic material solids loading can range from about 0.1 wt. % to about 60 wt. % based on the total weight of the medium (e.g., about 12 wt. % or less, or about 3 wt. % to about 12 wt. % in low-solids applications; about 12 wt. % to about 45 wt. % or about 27 wt. % to about 36 wt. % in high-solids applications).

The stillage, in whatever form, generally can be added to the lignocellulosic material in any suitable amount. Preferably, thin stillage is added to the aqueous hydrolysis medium such that the thin stillage represents at least some (or all) of the liquid portion of the aqueous medium. Suitable levels of stillage supplementation range from about 0.5 wt. % to about 100 wt. % relative to liquid portion of the aqueous medium, for example at about 10 wt. % or more, about 50 wt. % or more, about 10 wt. % to about 90 wt. %, or about 30 wt. % to about 70 wt. %. The non-stillage liquid portion of the aqueous medium generally includes water. For example, in an aqueous medium having a stillage supplementation of 50 wt. %, the liquid portion of the aqueous medium contains 50 wt. % water and 50 wt. % stillage (e.g., thin stillage). The stillage content relative to the aqueous medium as a whole can be equivalently expressed, taking into account the glucan/solids loading of the lignocellulosic material. For example, an aqueous medium having a stillage supplementation of 50 wt. % and a corn stover glucan loading of 6 wt. % includes: (1) about 6 wt. % corn stover glucan material, (2) about 12 wt. % corn stover non-glucan material, (3) about 41 wt. % stillage, (4) about 41 wt. % water, and (5) appropriate levels of hydrolytic enzymes. Thus, suitable levels of stillage in the aqueous medium range from about 0.5 wt. % to about 99 wt. % relative to the aqueous medium, for example at about 10 wt. % or more, about 40 wt. % or more, about 10 wt. % to about 90 wt. %, or about 25 wt. % to about 70 wt. %.

The stillage content of the aqueous medium also can be expressed in terms of the crude corn protein content of the aqueous medium (i.e., resulting from the addition of the stillage). Suitably, the crude protein content of the aqueous medium ranges from about 0.02 wt. % to about 5 wt. %. In various embodiments, the crude protein content can be at least about 0.05 wt. %, at least about 0.1 wt. %, at least about 0.2 wt. %, or at least about 0.3 wt. %. Additionally or alternatively, the crude protein content can be about 1.5 wt. % or less, about 2 wt. % or less, about 3 wt. % or less, or about 4 wt. % or less.

Preferably, the hydrolyzing enzymes include a combination of enzymes which hydrolyze the cellulose of the lignocellulosic material and (optionally) other complex carbohydrates (e.g., hemicellulose) to produce the sugars. Suitable combinations include (1) one or more cellulases and, optionally, (2) one ore more hemicellulases. The cellulase includes one or more enzymes that hydrolyze cellulose to form simpler sugars, also ultimately yielding glucose monosaccharides, for example endocellulase (endoglucanase), exocellulase (exoglucanase), and/or β-glucosidase (cellobiase). The hemicellulase includes one or more enzymes that hydrolyze hemicellulose to form simpler sugars, ultimately yielding monosaccharides (e.g., glucose, other hexoses, pentoses). Suitable hemicellulases include one or more of xyloglucanase, β-xylosidase, endoxylanase, α-L-arabinofuranosidase, α-glucuronidase, and acetyl xylan esterase. Preferably, the enzymes include a combination of both endo-enzymes (i.e., enzymes hydrolyzing internal polysaccharide bonds to form smaller poly- and oligosaccharides) and exo-enzymes (i.e., enzymes hydrolyzing terminal and/or near-terminal polysaccharide bonds to form mono-, di-, tri-, tetra-, etc. saccharides) to facilitate both the rapid hydrolysis of large polysaccharide molecules and the formation of monosaccharide glucose products. A suitable commercial cellulase/hemicellulase mixture is SPEZYME (available from Genencor, a division of Danisco, Copenhagen, Denmark) containing endoglucanase, exoglucanase, β-glucosidase, and hemicellulases (including xyloglucanase, β-xylosidase, endoxylanase, α-L-arabinofuranosidase, and α-glucuronidase). Another suitable commercial cellulase/hemicellulase mixture is ACCELERASE (Genencor/Danisco) containing endoglucanase, exoglucanase, βP-glucosidase, and hemicellulase. A suitable commercial β-glucosidase is NOVOZYM (available from Novozyme, Bagsvaerd, Denmark) containing primarily β-glucosidase and minor amounts of endoglucanase and exoglucanase.

The enzymes generally can be used in amounts that are not particularly limited. For example, cellulase, hemicellulase, or cellulase/hemicellulase mixtures individually can be used in amounts ranging from about 0.1 mg/g to about 500 mg/g (e.g., about 0.5 mg/g to about 200 mg/g, about 1 mg/g to about 100 mg/g, about 2 mg/g to about 50 mg/g, or about 3 mg/g to about 40 mg/g). The concentration units are milligrams of combined enzymes (e.g., combined amount of individual cellulase enzymes in a cellulase mixture) per gram of total glucan in the lignocellulosic material (e.g., glucose derivable from cellulose, and a portion of hemicellulose).

The lignocellulosic material is preferably pretreated at some point prior to its enzymatic hydrolysis. As illustrated in FIGS. 2-2 and 2-3, the pretreatment can be performed prior to adding the stillage to the lignocellulosic material; however, the pretreatment also can be performed on the mixture of the stillage and the lignocellulosic material. The pretreatment step disrupts the lignocellulosic material and increases the exposure of the carbohydrates inside the material, thereby facilitating the conversion of complex carbohydrates to simple sugars in the subsequent hydrolysis step. A wide variety of methods are suitable for pretreating lignocellulosic material to increase the yield of sugars for many different uses, for example including an ammonia fiber explosion (AFEX) process, a dilute-acid treatment process, a dilute-base treatment process, an ammonia recycle percolation process, a steam explosion process, a high-temperature exposure process, an irradiation process, a lime pretreatment process, an alkaline wet oxidation process, an ionic liquid pretreatment process, and combinations thereof. The goal of these pretreatments is to increase the rate and/or yield at which the sugars are obtained by chemical/biochemical means (e.g., acid catalysis, enzymatic catalysis, fermentation, animal digestion).

A preferred pretreatment method to improve the efficiency of the hydrolysis is the AFEX process (U.S. Pat. Nos. 4,600, 590 and 6,106,888). Ammonia and water are in contact with the lignocellulosic material under high pressure (e.g., 100-500 psi) and moderate temperatures (e.g., 50-200° C.) in an AFEX reaction vessel before rapidly releasing the pressure to destructure the plant material. AFEX decrystallizes cellulose, hydrolyzes hemicellulose, removes and depolymerizes lignin, and greatly increases the overall porosity of the biomass, thereby significantly increasing the rate of enzymatic hydrolysis.

Suitable ammonia concentrations range from about 0.1 g/g to 4 g/g (alternatively about 0.2 to 2, about 0.2 to 1, or about 0.5 to 1; units: g ammonia/g dry lignocellulosic material). Additional water also can be added to the AFEX reaction vessel; if done, suitable water contents range from about 0.1 g/g to 4 g/g (alternatively about 0.2 to 2, about 0.2 to 1, or about 0.4 to 1; units: g water/g dry lignocellulosic material). Similarly, suitable temperatures range from about 50° C. to about 200° C. (alternatively about 50° C. to about 150° C., about 50° C. to about 100° C., or about 70° C. to about 90° C.); however, even relatively low temperatures ranging from about 50° C. to about 60° C. can be used. The pretreatment of the lignocellulosic material in the AFEX reaction vessel reactor at such conditions causes the pressure in the vessel to increase (i.e., due to the heat-induced evaporation of water and ammonia into the reactor headspace). Generally, the generated pressure can range from about 100 psi to about 500 psi, although pressures ranging from about 100 psi to about 200 psi (e.g., about 150 psi) are often suitable. In an embodiment, the pressure in the reactor can selectively controlled with an external pressure control (e.g., by selectively releasing some gas prior to the explosive AFEX pressure release, by adjusting the interior volume of the reactor, and/or by adding an additional source gas to the reactor). Once the desired temperature and pressure have been obtained (e.g., about 20-25 min while the lignocellulosic material is heated and the ammonia is added to the reaction vessel), the reaction vessel is held for a time sufficient for reaction to occur, approximately 5 min (e.g., about 1 min to 20 min or about 2 min to 10 min). When the lignocellulosic material is pretreated under appropriate sets of these above-ambient pressure conditions, the structural carbohydrates in lignocellulosic material (cellulose and hemicellulose) become much more susceptible to hydrolysis by enzymes and acid. Following this pretreatment step at high ammonia concentrations, the pressure is released allowing much of the ammonia to evaporate and the system to cool. Additional ammonia can be removed by heating, stripping with inert gases, reducing the pressure and the like.

After pretreatment, the pH and temperature are adjusted to conditions suitable for enzymatic hydrolysis, and the resulting solids are hydrolyzed with enzymes to produce simple sugars and/or sugar oligomers having a desired molecular weight distribution as described above. The precise set of enzymatic activities used is tailored to generate the sugars (e.g., glucose, xylose, arabinose, mannose, etc. and their oligomers) at the desired concentrations and yields. Conventional cellulase mixtures used to hydrolyze acid-treated biomass may not be completely adequate for conversion of ammonia-treated biomass, since ammonia does not generate monomeric sugars as does acid. Proper hemicellulase activities can be used for hydrolysis of ammonia-treated biomass. Hydrolyzed solids containing adsorbed enzymes can be contacted with fresh, unhydrolyzed solids to recover and reuse a portion of the enzyme.

EXAMPLES

The following examples illustrate the disclosed compositions and methods, but are not intended to limit the scope of any claims thereto.

Example 1

Stillage Characterization

The following data relates to the analysis of thin stillage. Even though the majority of the solid portion of the whole stillage had been previously removed to form the thin stillage (e.g., as illustrated in FIGS. 2-2 and 2-3), the thin stillage still contained some residual solids. The liquid and solids from the thin stillage were separated by centrifugation (15 minutes and 3000 RPM). Then, the solid and liquid fractions were freeze dried and sent to Dairy One (Ithaca, N.Y.) for compositional analysis, as shown in Table 1. The solid fraction of the thin stillage was calculated to be 4% of the total weight.

TABLE 1

Thin Stillage Composition in Relation to Its Dry Matter and Total Weight

| Component | Solid % Dry Matter | Liquid % Dry Matter | Whole Thin Stillage % total weight |
| --- | --- | --- | --- |
| Crude Protein | 31.0 | 12.1 | 1.88 |
| Acid Detergent Fiber | 9.3 | nd | 0.37 |
| Neutral Detergent Fiber | 17.2 | nd | 0.69 |
| Non Fiber Carbohydrate | 24.7 | nd | 0.99 |
| Starch | 15.9 | 2.0 | 0.74 |
| Water Soluble Carbohydrates | 3.0 | 12.9 | 0.80 |
| Crude Fat | 25.4 | nd | 1.02 |
| Ash | 5.19 | nd | 0.21 |

Notes:
(1) "nd": not determined; and
(2) The percent dry matter solids and liquids in the whole thin stillage was 4% (total weight) and 4.8% (total weight) respectively.

Example 2

Stillage Supplementation of Pretreated Corn Stover

Example 2 analyzes the extent of improvement observed when thin stillage is used as a supplement during the enzymatic hydrolysis of lignocellulosic material (e.g., corn stover, with or without pretreatment). The whole thin stillage and the liquid fraction of the thin stillage were used separately as a supplement to a corn stover (AFEX-pretreated) enzymatic hydrolysis process.

AFEX Pretreatment: The raw lignocellulosic material (i.e., corn stover in this case) was first pretreated by an AFEX pretreatment process. The lignocellulosic material with 60 wt. % moisture (kg water/kg dry biomass) was transferred to a high-pressure Parr closed vessel reactor and liquid anhydrous ammonia (1 kg of ammonia/kg of dry biomass) was slowly charged to the vessel. The temperature was raised and maintained to a temperature of about 90° C. for a 5-minute residence time before explosively relieving the pressure. About 20-25 minutes elapsed while the lignocellulosic material was heated and ammonia was added to the reaction vessel; the residence time of about 5 minutes represents an additional constant-temperature hold time once the desired temperature was reached, resulting in a net AFEX-pretreatment time of about 25-30 minutes. Throughout the pretreatment process, the increasing temperature caused water and ammonia to vaporize, filling the reactor headspace and pressurizing the reactor to a pressure of about 150 psi (generally in the range of about 100 psi to about 200 psi). Once released, the instantaneous drop of pressure in the vessel caused the ammonia to vaporize, releasing the ammonia and resulting in an explosive decompression of the lignocellulosic material and considerable fiber disruption.

The NREL standard protocol (LAP-009) was followed for enzymatic hydrolysis of the lignocellulosic material. The lignocellulosic material was hydrolyzed at an industrially relevant high solids loading (glucan loading of 3% (w:v)) in a 0.05 molar citrate buffer solution (pH 4.8) at 50° C. with the following enzyme loading: 15 FPU/g glucan (~33 mg protein/g glucan) of SPEZYME CP (Genencor) cellulase, 64 p-NPGU/g glucan (~38 mg protein/g glucan) of β-glucosidase (NOVOZYM 188). "FPU" represents filter paper units, and "p-NPGU" represents p-nitrophenyl glycoside units.

Figure 4:
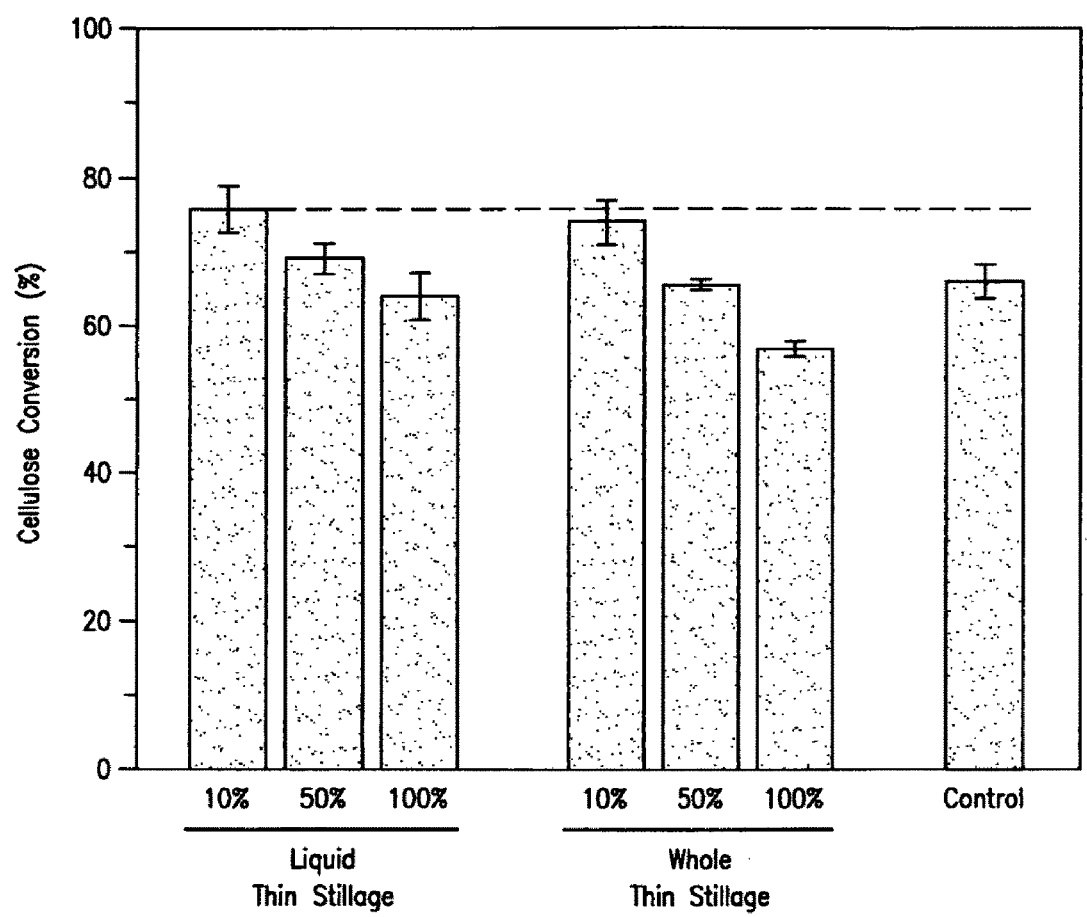
FIG. 4 is a graph illustrating the enhancement of glucan conversion in a corn stover enzymatic hydrolysis process (3% glucan loading) when using thin stillage supplementation.

Different percentages of thin stillage (liquid only or whole stillage) were studied. Before adding the enzymes, the mixture was incubated at 50° C. and 250 RPM for 1 hour. After adding the enzymes, a 72 hr enzymatic hydrolysis was performed at the same temperature and RPM, with samples being taken for sugar analysis at 72 hr. In order to know the effect of this supplement on the corn stover enzymatic hydrolysis conversion, a set of controls (without AFEX-treated biomass) were considered. The controls were important to know the fraction of glucan from the thin stillage that was converted to glucose. The results are shown in FIG. 4 and Table 2. According to the results, an increase in the glucan conversion during enzymatic hydrolysis was noticed when thin stillage was used as a supplement, in particular at lower-to mid-ranges of stillage supplementation. Additionally, stillage supplementation using liquid thin stillage was observed to be more effective than whole thin stillage (e.g., potentially due to inhibitory components in the solid portion of the whole thin stillage). The benefits of adding stillage to corn stover hydrolysis can be much more pronounced at higher solid loadings of about 9-12% where the enzyme inhibitions are higher.

TABLE 2

Glucan Conversion/Sugar Yield without Stillage Supplementation

| Stillage | Liquid Thin Stillage | | | Whole Thin Stillage | | | Control |
|---|---|---|---|---|---|---|---|
| Supplementation | 10% | 50% | 100% | 10% | 50% | 100% | 0% |
| Glucan Conversion | 76% | 69% | 64% | 74% | 66% | 57% | 67% |

TABLE 3

Glucan Conversion/Sugar Yield without Stillage Supplementation

| | Glucan Loading | | | |
|---|---|---|---|---|
| | 1% | 3% | 6% | 9% |
| Glucan Conversion | 94% | 75% | 64% | 53% |
| Glucose Yield | 11 g/l | 29 g/l | 54 g/l | 71 g/l |
| Xylose Yield | 5 g/l | 13 g/l | 22 g/l | 24 g/l |

The addition of stillage can be accomplished using several approaches, examples of which are illustrated in FIGS. 2-2 and 2-3. One approach (not shown) is the addition of the whole stillage before enzymatic hydrolysis. As presented in FIG. 2-2, only the thin stillage is added as a supplement during the enzymatic hydrolysis of lignocellulosic material (e.g., corn stover), and the wet grain is dried to produce DDGS as animal feed supplement. Another approach presented in FIG. 2-3 is the use of thin stillage as a supplement for enzymatic hydrolysis of lignocellulosic material, while the wet grain is dried until proper moisture is reached so it can be pretreated and also used as a glucan source for further enzymatic hydrolysis and fermentation along with the lignocellulosic material.

Comparative Example 1

Glucan Conversion without Stillage Supplementation

The effect of different glucan loadings (1%, 3%, 6%, and 9% (w:v)) on enzymatic hydrolysis and glucan conversion/yield for AFEX-treated corn stover was investigated in the absence of corn stillage supplementation.

The lignocellulosic material (i.e., corn stover in this case) was first pretreated by an AFEX pretreatment process under the same conditions as described in Example 2. The AFEX-pretreated material was then subjected to enzymatic hydrolysis. Similar to Example 2, the hydrolysis was performed at 50° C. and pH ~5 for 168 h with vigorous mixing at 250 RPM in a conical flask shaking incubator at variable glucan loadings. The enzyme loadings were: 33 mg protein/g glucan of cellulase (SPEZYME CP) and 31 mg protein/g glucan of β-glucosidase (NOVOZYM 188). The hydrolysis experiments were performed by batch-addition of the AFEX-treated corn stover at different time periods using pure water as the diluent for the hydrolysis medium (e.g., including the pretreated lignocellulosic material, enzymes, citrate buffer, and water).

Figure 5A:
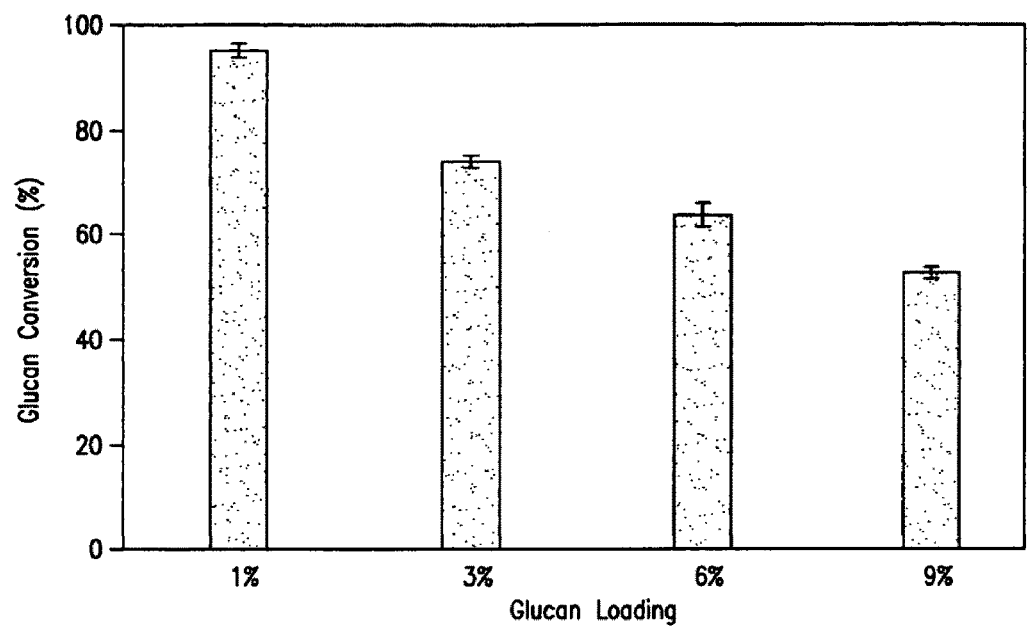
FIGS. 5a and 5b illustrate the glucan conversion (% of theoretical maximum) and sugar yield (g/l of glucose and xylose) for enzymatic hydrolysis batches at glucan loadings of 1%, 3%, 6%, and 9%.
Figure 5B:
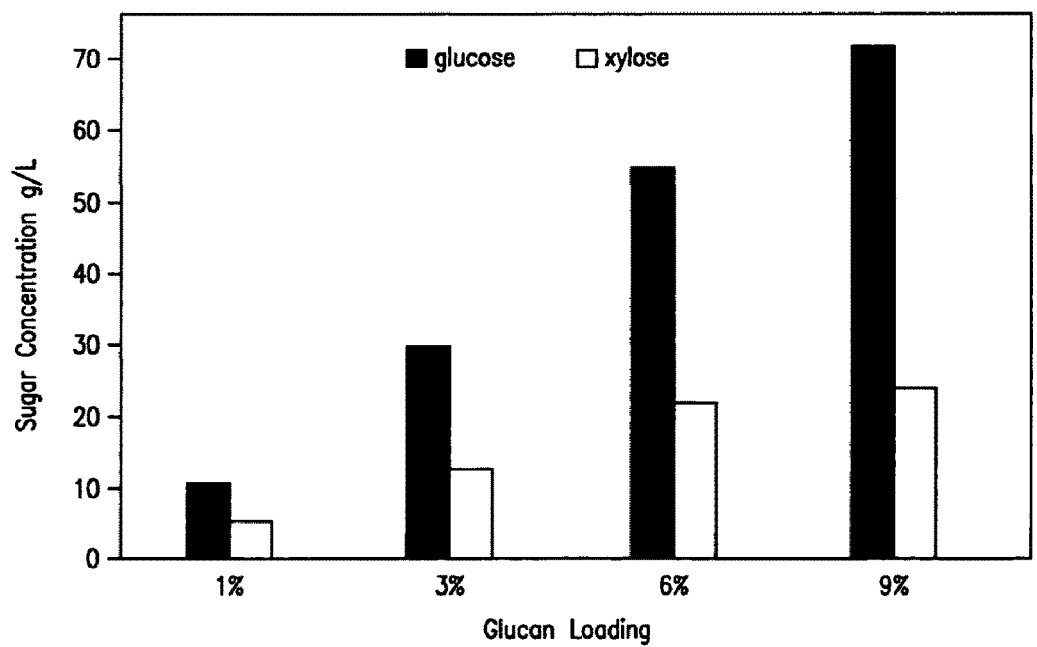

FIGS. 5a and 5b illustrate the glucan conversion (% of theoretical maximum) and sugar yield (g/l of glucose and xylose) for hydrolysis batches at glucan loadings of 1%, 3%, 6%, and 9%. The results illustrate the enzyme inhibition effects that are present at increasing glucan loadings. Specifically, the glucan conversion decreases as the glucan loading increases (FIG. 5a), meaning that the net throughput for a hydrolytic process cannot be linearly scaled up by simply increasing the glucan loading (FIG. 5b). For example, doubling the glucan loading from 3% to 6% only results in an 86% increase in the glucose yield (i.e., 54/29 ratio of glucose yield concentrations). The data from FIGS. 5a and 5b are summarized in Table 3.

Example 3

Glucan Conversion with Stillage Supplementation

The effect of different levels of stillage supplementation (0%, 10%, 50%, and 100%) on enzymatic hydrolysis and glucan conversion/yield for AFEX-treated corn stover was investigated in the presence of corn stillage supplementation and at a relatively high glucan loading (6% (w:v)).

The lignocellulosic material (i.e., corn stover in this case) was first pretreated by an AFEX pretreatment process under the same conditions as described in Example 2. The AFEX-pretreated material was then subjected to enzymatic hydrolysis. Similar to Example 2, the hydrolysis was performed at 50° C. and pH ~5 for 168 h with vigorous mixing at 250 RPM in a conical flask shaking incubator at variable glucan loadings. The enzyme loadings were: 33 mg protein/g glucan of cellulase (SPEZYME CP) and 31 mg protein/g glucan of β-glucosidase (NOVOZYM 188). The hydrolysis experiments were performed by batch-addition of the AFEX-treated corn stover at different time periods using a combination of pure water and/or the liquid portion of thin stillage (i.e., centrifuged thin stillage that is essentially free of solids) as the diluent for the hydrolysis medium (e.g., including the pretreated lignocellulosic material, enzymes, citrate buffer, and water/stillage medium).

Figure 6A:
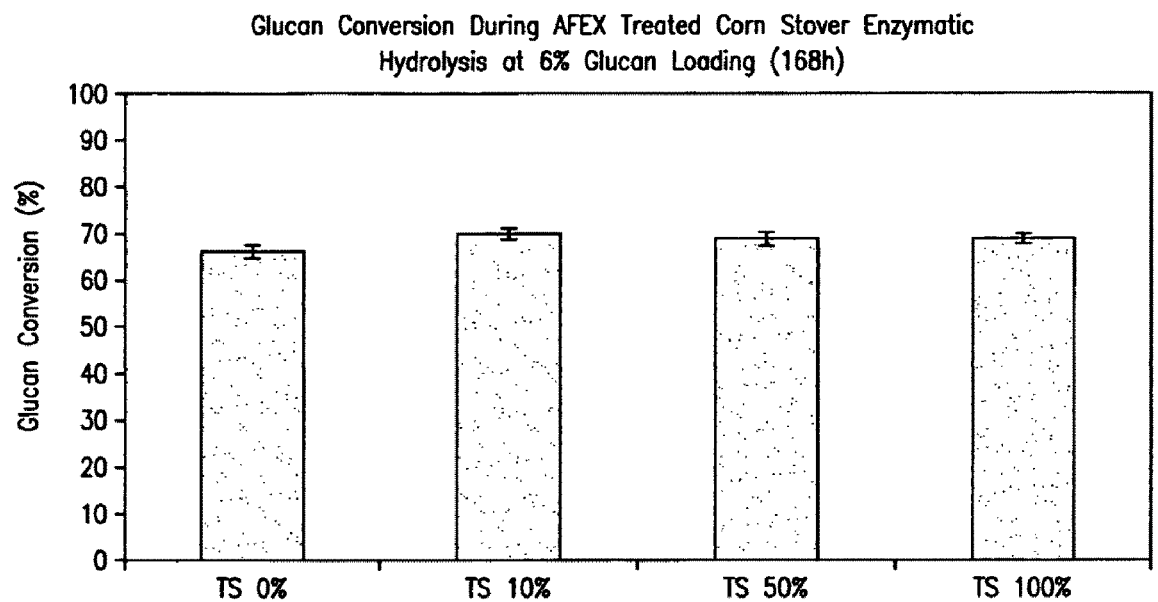
FIGS. 6a and 6b illustrate the glucan conversion (% of theoretical maximum) and sugar yield (g/l of glucose) for enzymatic hydrolysis batches at stillage loadings of 0%, 10%, 50%, and 100%.
Figure 6B:
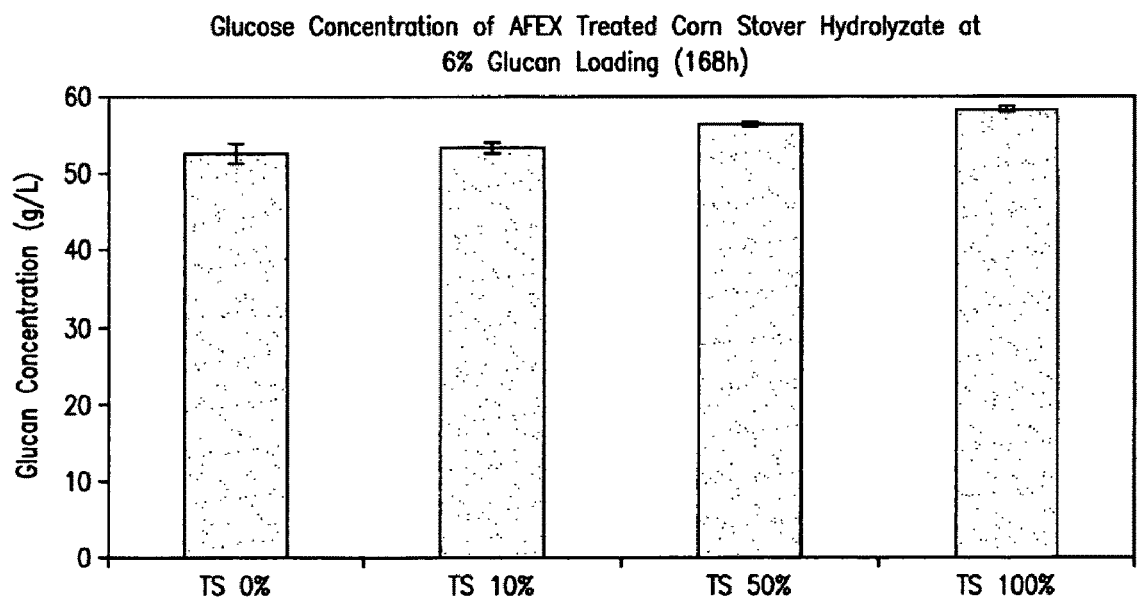

FIGS. 6a and 6b illustrate the glucan conversion (% of theoretical maximum) and sugar yield (g/l of glucose) for hydrolysis batches at stillage supplementation levels of 0%, 10%, 50%, and 100%. Specifically, in the figures, "TS 0%" indicates a 0% replacement of water with stillage (i.e., no stillage was used and the hydrolysis was essentially the same as in Comparative Example 1), "TS 10%" indicates a 10% replacement of water with stillage (i.e., the hydrolysis medium diluent was 10/90 (v/v) mixture of thin stillage and water), "TS 50%" indicates a 50% replacement of water with stillage, and "TS 100%" indicates a 100% replacement of water (i.e., the hydrolysis medium diluent was entirely thin stillage). Control experiments were performed on similar conditions just using thin stillage (i.e., without any lignocellulosic material), and the glucose amount was subtracted from the corn stover hydrolysis supplementation data. An improvement of about 5% in glucan conversion was observed for corn stover hydrolysis performed using 100% thin stillage, and the improvement is due the protein present in the thin stillage. Similarly, the stillage supplementation improves the scalability of the hydrolytic process. For example, the glucose yield of a 3% glucan loading is 29 g/l without stillage supplementation (Table 3). However, doubling glucose loading to 6% using 100% stillage supplementation results in a glucose yield of 59 g/l (Table 4; representing a 103% increase relative to the 29 g/l at 3% glucan loading without stillage supplementation). The data from FIGS. 6a and 6b are summarized in Table 4.

TABLE 4

Glucan Conversion/Sugar Yield with Stillage Supplementation

|  | Thin Stillage Supplementation | | | |
|---|---|---|---|---|
|  | 0% | 10% | 50% | 100% |
| Glucan Conversion | 64% | 70% | 69% | 69% |
| Glucose Yield | 53 g/l | 54 g/l | 57 g/l | 59 g/l |

Example 4

Ethanol Yield with Stillage Supplementation

The ethanol yield from the four enzymatically hydrolyzed corn stover samples of Example 3 (i.e., at stillage supplementation levels of 0%, 10%, 50%, and 100%) was investigated. The yeast *Saccharomyces cerevisiae* (strain 424A (LNH-ST); available from the Laboratory of Renewable Resources Engineering, Purdue University) was used to ferment the glucose and xylose in the hydrolyzed corn stover samples, and the ethanol yield was measured as a function of time. The fermentation was performed in a fermentation vessel containing the hydrolyzed corn stover (i.e., which contained a predetermined level of stillage supplementation) at a temperature of 30° C. and a yeast concentration of about 0.2 wt. % (relative to the fermentation medium) for a total fermentation time of about 132 hours.

Figure 7A:
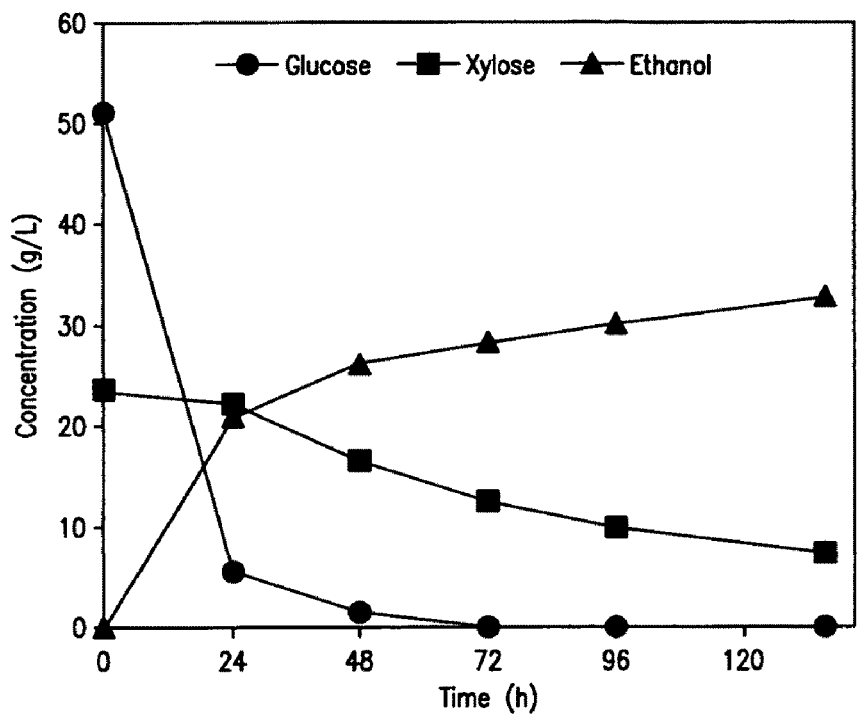
FIGS. 7a-7d show results of fermentation over time for four enzymatically hydrolyzed corn stover samples supplemented with stillage.
Figure 7B:
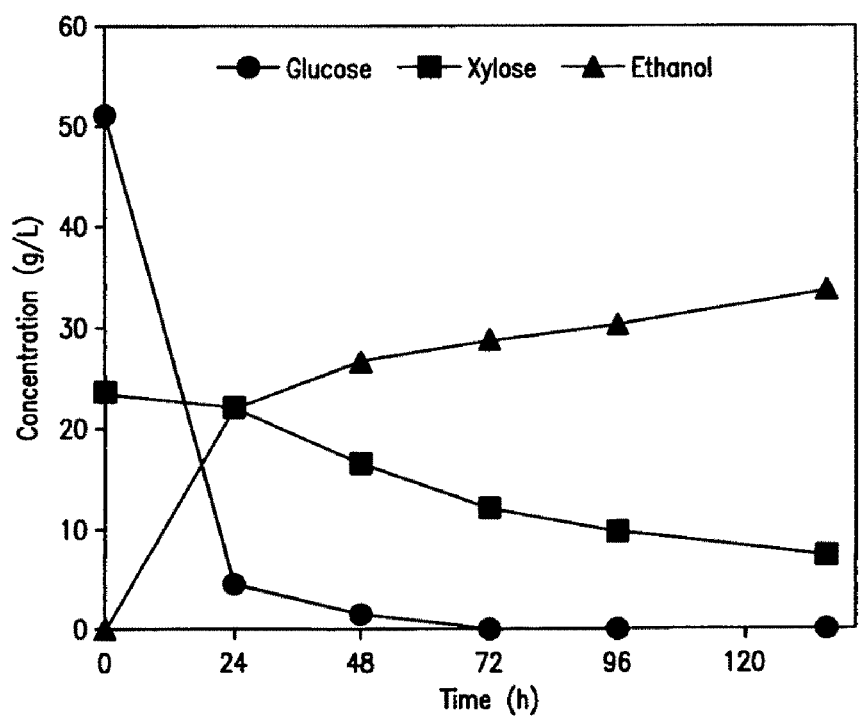
Figure 7C:
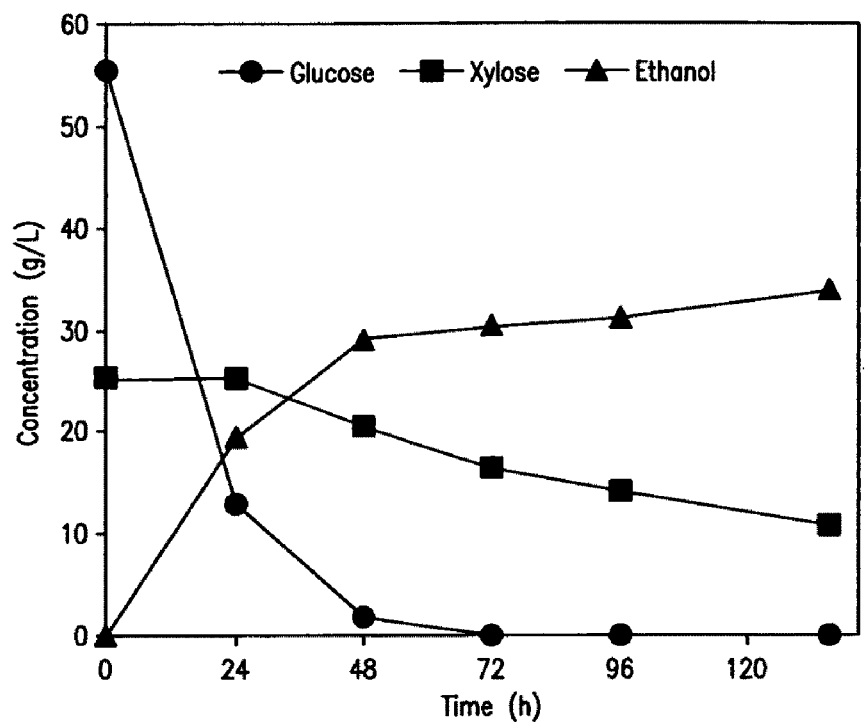
Figure 7D:
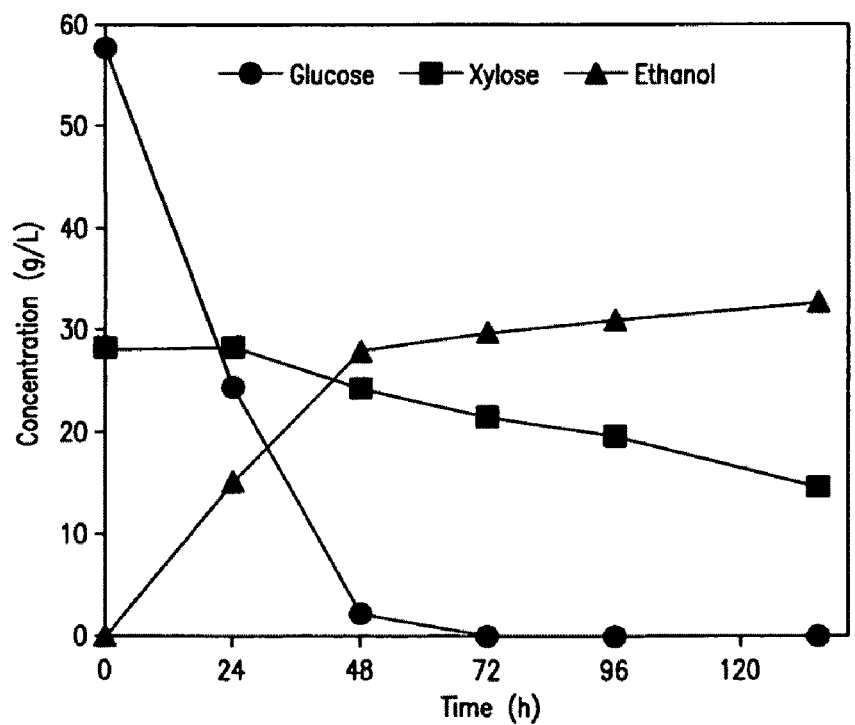

The results of the fermentation are provided in FIGS. 7a-7d and Table 5. In Table 5, "Initial Sugar" and "Residual Sugar" represent the combined glucose and xylose concentrations at the onset of fermentation and after 132 hours of fermentation, respectively. "Ethanol" represents the ethanol concentration after 132 hours of fermentation. "Metabolic Yield" represents the amount of sugar metabolized relative to the theoretical ethanol yield. "Productivity" represents an average rate of ethanol production determined at a fermentation time of 72 h. The data illustrate the improved rate of ethanol production when using stillage supplementation. From Table 5, the average productivity of about 0.41 g/L/h for stillage supplementation levels ranging from about 10% to 100% represents about a 5% increase in ethanol productivity in the absence of stillage supplementation (i.e., at about 0.39 g/L/h). From FIGS. 7a-7d, the ethanol concentration more rapidly reaches a threshold level of 30 g/L when using stillage supplementation than without stillage supplementation. Additionally, there may be some fermentation inhibition at higher levels of stillage supplementation (e.g., as illustrated in FIGS. 7c and 7d by the lower rate of glucose and xylose consumption at 100% stillage supplementation as compared to 50% stillage supplementation). Accordingly, it may be desirable in some embodiments to use less than 100% stillage supplementation and/or to pre-treat the stillage to remove/reduce any inhibitory components of the stillage.

TABLE 5

Sugar Conversion/Ethanol Yield with Stillage Supplementation

|  | Thin Stillage Supplementation | | | |
|---|---|---|---|---|
|  | 0% | 10% | 50% | 100% |
| Initial sugar (g/L) | 74.55 | 74.53 | 80.71 | 85.99 |
| Residual sugar (g/L) | 7.41 | 7.27 | 10.83 | 14.54 |
| Ethanol (g/L) | 32.86 | 33.44 | 33.73 | 32.62 |
| Metabolic yield (%) | 95.98 | 97.47 | 94.64 | 89.52 |
| Productivity (g EtOH/L/h) | 0.39 | 0.40 | 0.42 | 0.41 |

According to the disclosure corn grain stillage or any of its components (e.g., whole stillage, thin stillage, liquid portion of the thin stillage, residual solid portion of the thin stillage) is used as a supplement for lignocellulosic material (e.g., corn stover) hydrolysis. The lignocellulosic material can be pretreated by any of the leading pretreatment technologies.[6] Overall, the technology benefits the whole dry mill process and substantially reduces energy costs as necessitated by previously reported processes.[7-9] Specifically, the disclosed methods reduce water usage (e.g., thin stillage can be used at least partially in place of fresh water used to form an aqueous hydrolysis medium). Additionally, utilizing the water content of the stillage can substantially reduce the heat/energy demand of a process that would otherwise require energy to reduce the water content of the stillage (e.g., when producing DDGS as a co-product of a corn ethanol process). Also, a high solids loading (e.g., up to 12% glucan) while adding the stillage during the hydrolysis process can be used. The stillage can be added to a variety of lignocellulosics like corn stover, miscanthus, rice straw, poplar, and bagasse. The stillage also can improve fermentation. Pre-treating wet distiller's grains at different moisture contents can be used in the presence and absence of stillage. Adding stillage during hydrolysis can be used to improve process economics compared with adding water alone.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

REFERENCES

1. U.S. Renewable Fuels Association website—Fuel Ethanol Industry Bio-Refineries and Production Capacity, dated Mar. 27, 2007.
2. Bothast, R. J. and Schlicher, M. A., Biotechnological processes for conversion of corn into ethanol, Appl. Microbiol Biotechnol., 67: 19-25 (2005).
3. Hahn-Hägerdal B, Galbe M, Gorwa-Grauslund M F, Liden G, and Zacchi G, Bio-ethanol—the fuel of tomorrow from the residues of today, Trends in Biotech., vol. 24, no. 12, p. 549-556 (2006).
4. Gray K A, Zhao L, and Emptage M, Bioethanol. Current Opinion in Chemical Biology 10:141-146 (2006);
5. Wheals A E, Basso L C, Alves D M G and Amorim H V, Fuel ethanol after 25 years, TIBTECH, 17:482-487 (1999).
6. Mosier N, Wyman C, Dale B, Elander R, Lee Y Y, Features of promising technologies for pretreatment of lignocellulosic biomass, Bioresource Technol. 96, 673-686 (2005).

7. Rajagopalan S, Ponnampalam, McCalla D and Stowers M, Enhancing Profitability of Dry Mill Ethanol Plants, Appl. Biochem. Biotechnol, 120, 37-50 (2004).
8. Rausch K D and Belyea R L, The future of co-products from corn processing. Appl. Biochem. Biotechnol. 128, 47-86 (2006).
9. Belyea R L, Clevenger T E, Shingh V, Tumbleson M E and Rausch K D, Element Concentrations of Dry-Grind Corn-Processing streams, Appl. Biochem. Biotechnol. 134, 113-128 (2006).

What is claimed is:

1. A process for producing sugars from a lignocellulosic material and corn comprising:
    pretreating the lignocellulosic material with an ammonia treatment process to produce a pretreated lignocellulosic material, wherein ammonia in the ammonia pretreatment process is present in a concentration ranging from about 0.2 to about 4 grams ammonia per gram of the lignocellulosic material;
    separating corn grain stillage into a substantially liquid fraction comprising about 0.05 wt. % to about 50 wt. % crude protein and a substantially solid fraction;
    adding the substantially liquid fraction to the pretreated lignocellulosic material; and
    hydrolyzing complex carbohydrates in the pretreated lignocellulosic material in an aqueous medium with one or more hydrolyzing enzymes to form the sugars, wherein the substantially liquid fraction comprises some or all of the aqueous medium.

2. The process of claim 1, wherein the corn grain stillage comprises whole corn grain stillage with solids.

3. The process of claim 1, wherein the corn grain stillage comprises thin corn grain stillage.

4. The process of claim 1, wherein the lignocellulosic material comprises corn stover.

5. The process of claim 1, wherein the lignocellulosic material comprises one or more of miscanthus, rice straw, poplar, and bagasse.

6. The process of claim 1, wherein the hydrolyzing is performed in an aqueous medium which contains the pretreated lignocellulosic material, the corn grain stillage, and the one or more hydrolyzing enzymes, wherein the pretreated lignocellulosic material comprises glucan and the aqueous medium has a glucan loading as a component of the pretreated lignocellulosic material ranging from about 0.1 wt. % to about 20 wt. %.

7. The process of claim 1, wherein the hydrolyzing is performed in an aqueous medium which contains the pretreated lignocellulosic material, the corn grain stillage, and the one or more hydrolyzing enzymes, wherein the aqueous medium comprises about 0.5 wt. % to about 99 wt. % corn grain stillage relative to the aqueous medium.

8. A process for producing sugars from a lignocellulosic material and corn comprising:
    pretreating the lignocellulosic material with an ammonia treatment process to produce a pretreated lignocellulosic material, wherein ammonia in the ammonia pretreatment process is present in a concentration ranging from about 0.2 to about 4 grams ammonia per gram of the lignocellulosic material;
    separating corn grain stillage into a protein-containing thin stillage component and a wet grain component;
    adding the protein-containing thin stillage component to the pretreated lignocellulosic material; and
    hydrolyzing complex carbohydrates in the pretreated lignocellulosic material with one or more hydrolyzing enzymes to form the sugars, wherein the hydrolyzing is performed in an aqueous medium which contains the pretreated lignocellulosic material, the protein-containing thin stillage component, and the hydrolyzing enzymes, wherein the aqueous medium comprises about 0.02 wt. % to about 5 wt. % crude corn protein as a component of the protein-containing thin stillage component relative to the aqueous medium.

9. The process of claim 8, wherein the one or more hydrolyzing enzymes comprise one or more cellulases and, optionally, one or more hemicellulases.

10. The process of claim 8, wherein the pretreating causes hemicellulose and cellulose in the complex carbohydrates to become more accessible to hydrolysis.

11. The process of claim 8, wherein the ammonia treatment process is an ammonia fiber expansion process.

12. The process of claim 10, wherein the pretreating further comprises performing an additional pretreatment process selected from a dilute-acid treatment process, a dilute-base treatment process, an ammonia recycle percolation process, a steam explosion process, a high-temperature exposure process, an irradiation process, a lime pretreatment process, an alkaline wet oxidation process, and an ionic liquid pretreatment process and combinations thereof.

13. The process of claim 8, wherein the process further comprises:
    drying the substantially solid portion to form distillers dried grains with solubles (DDGS).

14. The process of claim 8, further comprising fermenting the sugars.

15. The process of claim 14, wherein the hydrolyzing of the complex carbohydrates in the pretreated lignocellulosic material and the fermenting of the sugars are performed in a single vessel.

16. A process for producing sugars from corn stover comprising:
    pretreating the corn stover to produce pretreated corn stover, wherein the pretreating is performed with an ammonia treatment process which causes hemicellulose and cellulose in the corn stover to become more accessible to hydrolysis, wherein ammonia in the ammonia treatment process is present in a concentration ranging from about 0.2 to about 4 grams ammonia per gram of the lignocellulosic material;
    adding thin corn grain stillage to an aqueous medium containing the pretreated corn stover, wherein the thin corn grain stillage comprises crude corn protein and the aqueous medium comprises about 0.5 wt. % to about 99 wt. % thin corn grain stillage relative to the aqueous medium; and
    hydrolyzing the hemicellulose and cellulose in the aqueous medium with one or more hydrolyzing enzymes to form the sugars.

17. The process of claim 16, wherein the pretreated corn stover comprises glucan and the aqueous medium has a glucan loading as a component of pretreated corn stover ranging from about 1 wt. % to about 4 wt. %.

18. The process of claim 16, wherein the pretreated corn stover comprises glucan, and the aqueous medium has a glucan loading as a component of pretreated corn stover ranging from about 4 wt. % to about 15 wt. %.

19. The process of claim 16, further comprising fermenting the sugars.

20. A process for producing sugars from a lignocellulosic material and corn comprising:
    pretreating the lignocellulosic material with an ammonia treatment process to produce a pretreated lignocellulosic material, wherein ammonia in the ammonia pretreatment process is present in a concentration ranging from about 0.2 to about 4 grams ammonia per gram of the lignocellulosic material;
adding corn grain stillage to the pretreated lignocellulosic material, wherein the corn grain stillage comprises crude corn protein; and
in an aqueous medium, hydrolyzing complex carbohydrates in the pretreated lignocellulosic material with one or more hydrolyzing enzymes to form sugars, wherein the aqueous medium contains the pretreated lignocellulosic material, the corn grain stillage, and the one or more hydrolyzing enzymes, further wherein the aqueous medium comprises about 0.5 wt. % to about 99 wt. % corn grain stillage relative to the aqueous medium.

21. The method of claim 20 wherein the corn grain stillage comprises at least 0.1% corn grain protein.

22. The method of claim 20 wherein the corn grain stillage comprises about 0.1% to about 10% corn grain protein.

23. The method of claim 1 wherein the corn grain stillage comprises about 0.1% corn grain protein.

24. The method of claim 1 wherein the corn grain stillage comprises about 0.5% to about 10% corn grain protein.

25. The method of claim 1 wherein the corn grain stillage comprises about 1% corn grain protein.

26. The method of claim 1 wherein the corn grain stillage comprises about 1% to about 4% corn grain protein.

27. The method of claim 26 wherein the corn grain stillage comprises about 2% corn grain protein.

28. The method of claim 1 wherein the ammonia in the ammonia pretreatment process is present in a concentration ranging from about 0.2 to about 2 grams ammonia per gram of the lignocellulosic material.

29. The method of claim 28 wherein the ammonia in the ammonia pretreatment process is present in a concentration ranging from about 0.5 to about 1 grams ammonia per gram of the lignocellulosic material.

* * * * *